(12) United States Patent
Katuin et al.

(10) Patent No.: US 12,714,798 B2
(45) Date of Patent: Aug. 25, 2026

(54) DOSE DETECTION WITH PIEZOELECTRIC SENSING FOR A MEDICATION DELIVERY DEVICE

(71) Applicant: Eli Lilly and Company, Indianapolis, IN (US)

(72) Inventors: Joseph Edward Katuin, Cicero, IN (US); Sean Matthew Pszenny, Cambridge, MA (US)

(73) Assignee: Eli Lilly and Company, Indianapolis, IN (US)

( * ) Notice: Subject to any disclaimer, the term of this patent is extended or adjusted under 35 U.S.C. 154(b) by 58 days.

(21) Appl. No.: 18/165,443

(22) Filed: Feb. 7, 2023

(65) Prior Publication Data

US 2023/0173189 A1 Jun. 8, 2023

Related U.S. Application Data

(63) Continuation of application No. 16/637,355, filed as application No. PCT/US2018/047442 on Aug. 22, 2018, now Pat. No. 11,612,698.

(Continued)

(51) Int. Cl.
*A61M 5/315* (2006.01)

(52) U.S. Cl.
CPC .... *A61M 5/31551* (2013.01); *A61M 5/31558* (2013.01); *A61M 2205/0294* (2013.01);

(Continued)

(58) Field of Classification Search
CPC .......... A61M 5/31551; A61M 5/31558; A61M 5/31593; A61M 5/31581; A61M 5/31585;

(Continued)

(56) References Cited

U.S. PATENT DOCUMENTS 6,277,099 B1 8/2001 Strowe et al.
6,485,465 B2 11/2002 Moberg et al.

(Continued)

FOREIGN PATENT DOCUMENTS

CN 101107030 A 1/2008
CN 101516421 A 11/2012

(Continued)

OTHER PUBLICATIONS

Patent Cooperation Treaty International Search Report pertaining to International Application No. PCT/US2018/047442; International Filing Date: Aug. 22, 2018; Date of Mailing: Dec. 19, 2018.

(Continued)

*Primary Examiner* — Chelsea E Stinson
(74) *Attorney, Agent, or Firm* — Arthur Shum

(57) ABSTRACT

The present disclosure relates to a medication delivery device having a dose detection system and an associated control system configured to determine an amount of medication delivered from the medication delivery device based on the sensing of relative rotation within the medication delivery device. The relative rotation may occur between a dose setting member and an actuator and/or housing of the medication delivery device. The rotation sensing may involve piezoelectric sensing, more specifically repeatedly deforming a piezoelectric sensor with a mechanical force. The dose detection system may be a modular or integral component of the medication delivery device.

5 Claims, 24 Drawing Sheets

Related U.S. Application Data

(60) Provisional application No. 62/552,659, filed on Aug. 31, 2017.

(52) U.S. Cl.
CPC ............... *A61M 2205/3327* (2013.01); *A61M 2205/3553* (2013.01)

(58) Field of Classification Search
CPC .......... A61M 5/31586; A61M 5/31575; A61M 5/3158; A61M 2205/0294; A61M 2205/3327; A61M 2205/3553; A61M 2205/3561
See application file for complete search history.

(56) References Cited

U.S. PATENT DOCUMENTS

| | | | | |
|---|---|---|---|---|
| 7,138,806 | B2 | 11/2006 | Gafner et al. | |
| 8,560,271 | B2 | 10/2013 | Koehler et al. | |
| 8,632,509 | B2 | 1/2014 | Møller et al. | |
| 2007/0151390 | A1 | 7/2007 | Blumenkranz et al. | |
| 2010/0145656 | A1 | 6/2010 | Koehler et al. | |
| 2011/0313350 | A1 | 12/2011 | Krulevitch et al. | |
| 2014/0005950 | A1 | 1/2014 | Groeschke et al. | |
| 2017/0182258 | A1 | 6/2017 | Michael | |
| 2019/0209783 | A1 | 7/2019 | Utermoehlen et al. | |
| 2019/0269859 | A1* | 9/2019 | Jacobsen | A61M 5/31551 |
| 2023/0001095 | A1* | 1/2023 | Antonelli | A61M 5/31551 |

FOREIGN PATENT DOCUMENTS

| | | |
|---|---|---|
| EP | 1074273 | 2/2001 |
| EP | 2182456 | 5/2010 |
| EP | 2221079 | 8/2010 |
| JP | 2001087386 | 4/2001 |
| JP | 2011519599 | 7/2011 |
| WO | 9526769 | 10/1995 |
| WO | 2006116997 | 11/2006 |
| WO | 09132777 | 11/2009 |
| WO | 2017198809 | 11/2017 |
| WO | 2018078178 | 5/2018 |

OTHER PUBLICATIONS

Patent Cooperation Treaty Written Opinion of the International Searching Authority pertaining to International Application No. PCT/US2018/047442; International Filing Date: Aug. 22, 2018; Date of Mailing: Dec. 19, 2018.

Office action issued by the Japanese Patent Office on Jan. 26, 2021 pertaining to Japanese Patent Application 2020-505196.

Office action issued by the Japanese Patent Office on Jun. 7, 2022 pertaining to Japanese Patent Application 2021-096342.

Office action issued on Mar. 9, 2022 by the Chinese Patent Office pertaining to Chinese Patent Application No. 201880056505.6 (machine translation provided).

* cited by examiner

DOSE DETECTION WITH PIEZOELECTRIC SENSING FOR A MEDICATION DELIVERY DEVICE

CROSS REFERENCE TO RELATED APPLICATIONS

This application claims priority to U.S. Provisional Patent Application Ser. No. 62/552,659, filed Aug. 31, 2017, the disclosure of which is hereby expressly incorporated by reference herein in its entirety.

TECHNICAL FIELD

The present disclosure relates to an electronic dose detection system for a medication delivery device, and illustratively to an electronic dose detection module or integrated dose detection system with piezoelectric sensing to detect a dose of medication delivered by the delivery device.

BACKGROUND

Patients suffering from various diseases must frequently inject themselves with medication. To allow a person to conveniently and accurately self-administer medicine, a variety of devices broadly known as injector or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many injector pens and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device and detects the relative movement of a sensed component secured to a second member of the device.

The administration of a proper amount of medication requires that the dose delivered by the medication delivery device be accurate. Many injector pens and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by measuring mechanical parts which directly correspond to the dose displayed in the dose window to the user of the medication delivery device during an injection event. Further, in certain embodiments, there is a need for such a dose detection device to be removable and reusable with multiple delivery devices. In other embodiments, there is a need for such a dose detection device to be integral with the delivery device.

SUMMARY

The present disclosure relates to a medication delivery device having a dose detection system and an associated control system configured to determine an amount of medication delivered from the medication delivery device based on the sensing of relative rotation within the medication delivery device. The relative rotation may occur between a dose setting member and an actuator and/or housing of the medication delivery device. The rotation sensing may involve piezoelectric sensing, more specifically repeatedly deforming a piezoelectric sensor with a mechanical force. The dose detection system may be a modular or may be an integral component of the medication delivery device.

In accordance with a first aspect of the present disclosure, a medication delivery device is provided including a device body having a longitudinal axis, an actuator that rotates relative to the device body during a dose setting operation and moves axially relative to the device body along the longitudinal axis during a dose dispensing operation to deliver a medication, a dose setting member that rotates relative to the device body during both the dose setting and dose dispensing operations, and a dose detection system configured to detect rotation of the dose setting member relative to the actuator during the dose dispensing operation, the dose detection system including a piezoelectric sensor.

In accordance with a second aspect of the present disclosure, a medication delivery device is provided including a device body having a longitudinal axis, an actuator that rotates relative to the device body during a dose setting operation and moves axially relative to the device body along the longitudinal axis during a dose dispensing operation to deliver a medication, a dose setting member that is fixedly coupled to the actuator during the dose setting operation and that rotates relative to the actuator during the dose dispensing operation, and a piezoelectric sensor configured to detect rotation between the dose setting member and the actuator during the dose dispensing operation.

In accordance with a third aspect of the present disclosure, a medication delivery device is provided including a device body having a longitudinal axis, a dose setting member coupled to the device body and rotatable relative to the device body during a dose dispensing operation, an actuator coupled to the device body and movable relative to the device body during the dose dispensing operation, and a dose detection system configured to detect rotation of the dose setting member during the dose dispensing operation. The dose detection system includes at least one deformable member, a piezoelectric sensor coupled to the at least one deformable member, and at least one force applicator configured to apply a mechanical force to the at least one deformable member and deform the piezoelectric sensor during the dose dispensing operation.

The dose detection systems described herein have the advantage that they are measuring mechanical parts which directly correspond to the dose displayed in the dose window to the user of the medication delivery device.

BRIEF DESCRIPTION OF THE DRAWINGS

The features and advantages of the present disclosure will become more apparent to those skilled in the art upon consideration of the following detailed description taken in conjunction with the accompanying figures.

DETAILED DESCRIPTION

Figure 1:
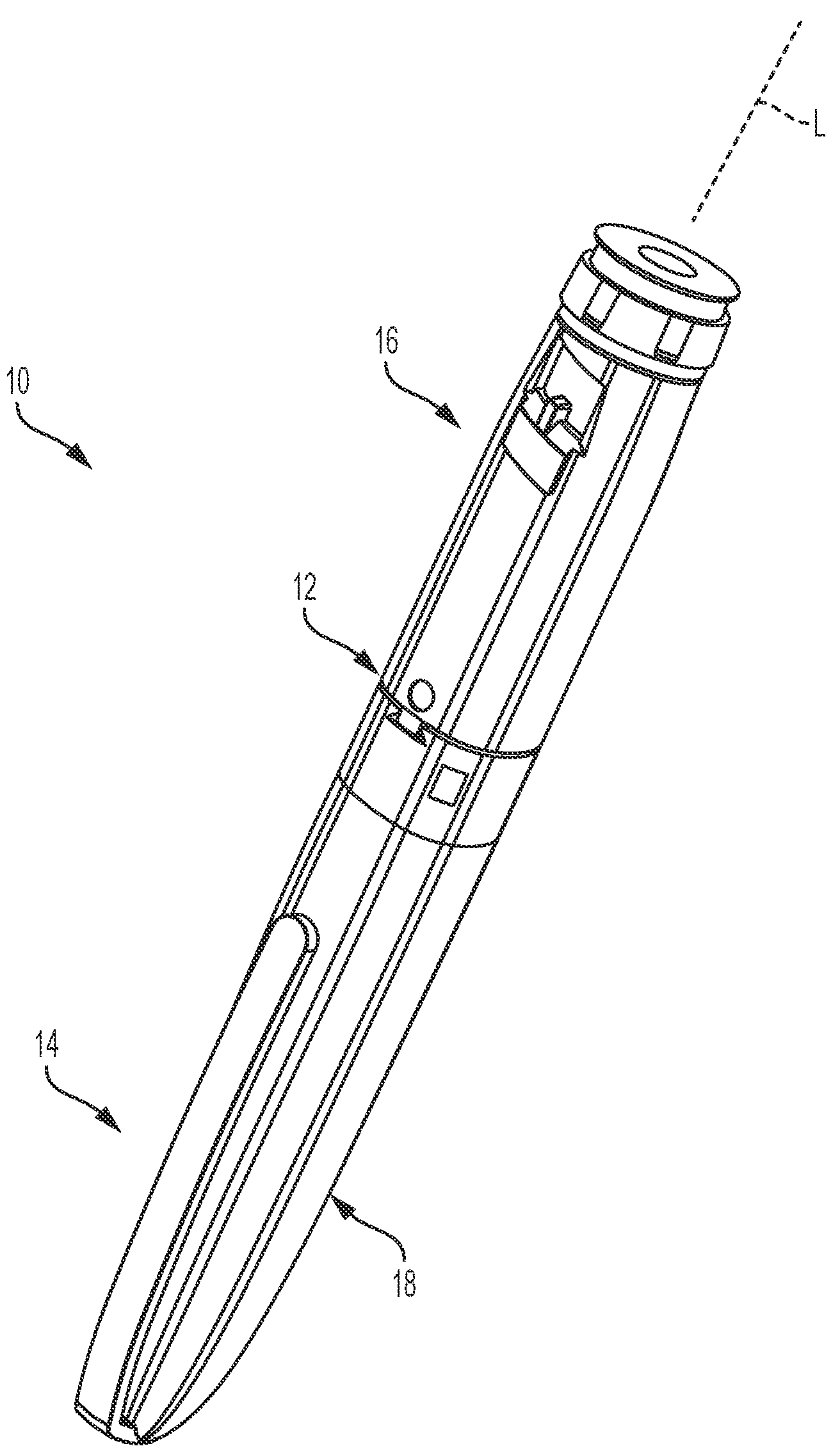
FIG. 1 is a perspective view of an exemplary medication delivery device of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

An exemplary medication delivery device 10 is illustrated in FIGS. 1-4 as an injector pen configured to inject a medication into a patient through a needle 24. Although the illustrative medication delivery device 10 is an injector pen, the medication delivery device 10 may be any device which is used to set and to deliver a dose of a medication, such as an infusion pump, bolus injector or an auto injector device. The medication may be of any type that may be delivered by such a medication delivery device 10.

Figure 2:
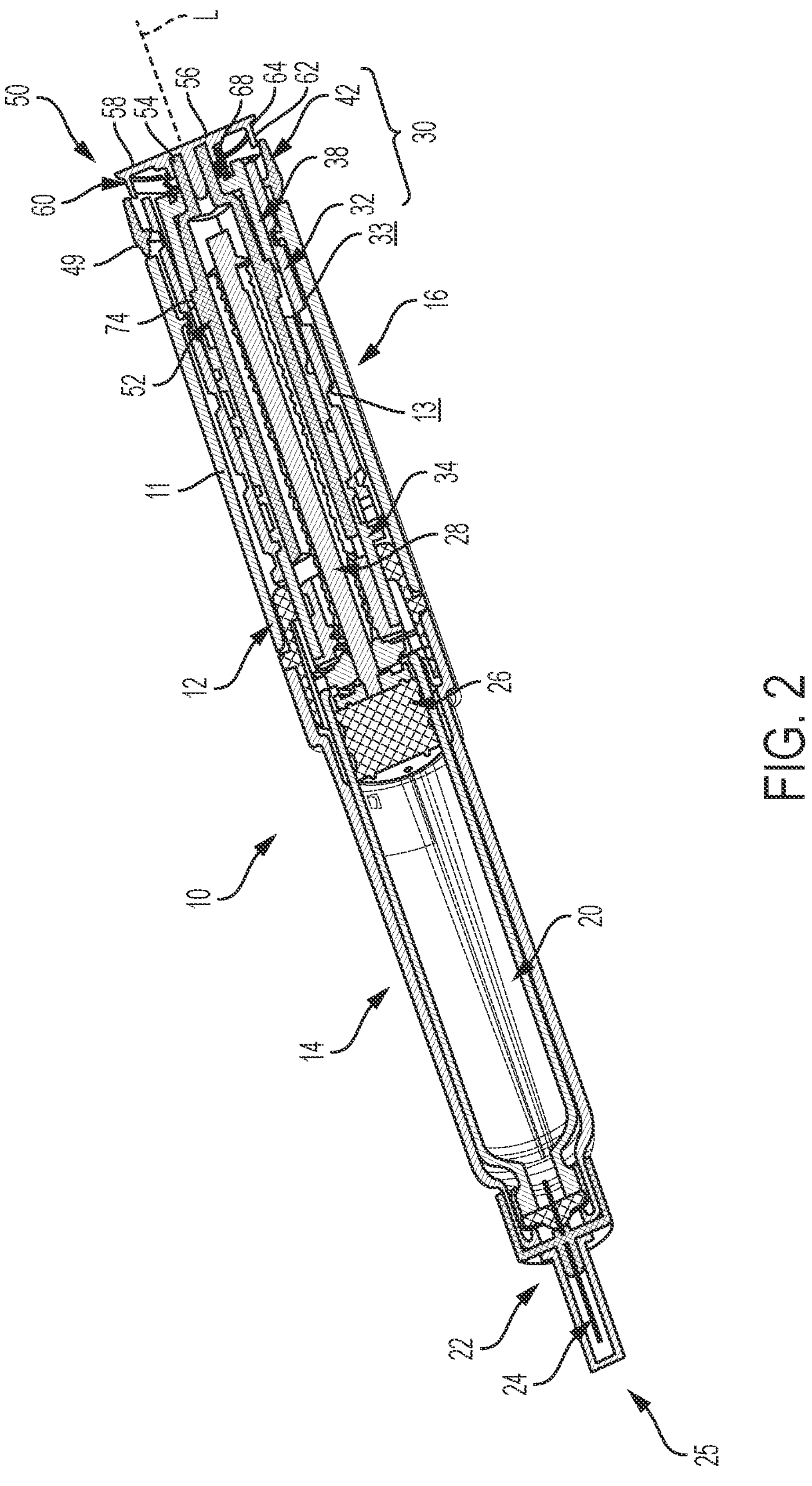
FIG. 2 is a cross-sectional perspective view of the exemplary medication delivery device of FIG. 1.

Medication delivery device 10 includes a body 11 comprising an elongated, pen-shaped housing 12 including a distal portion 14 and a proximal portion 16 arranged along a longitudinal axis L. Distal portion 14 is receivable within a pen cap 18. Referring to FIG. 2, distal portion 14 includes a reservoir or cartridge 20 configured to hold the medication to be dispensed through its distal outlet end 25 during a dispensing operation.

Devices described herein, such as a device 10, may further comprise the medication, such as for example, within the reservoir 20. In another embodiment, a system may comprise one or more devices including, for example, device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

The outlet end 25 of distal portion 14 is equipped with a removable needle assembly 22 including the injection needle 24. A piston 26 is positioned in fluid reservoir 20. An injecting mechanism or drive member 28, illustratively a screw, is positioned in proximal portion 16 and is axially moveable relative to housing 12 along longitudinal axis L to advance piston 26 toward the outlet end 25 of reservoir 20 during the dose dispensing operation to force the contained medicine through the needled outlet end 25.

A dose setting member 30 is coupled to housing 12 for setting a dose amount to be dispensed by device 10. In the illustrated embodiment, dose setting member 30 is in the form of a screw element operative to spiral (i.e., simultaneously move axially along longitudinal axis L and rotationally about longitudinal axis L) relative to housing 12 during dose setting and dose dispensing operations. FIGS. 1 and 2 illustrate the dose setting member 30 fully screwed into housing 12 at its home or zero position. Dose setting member 30 is operative to screw out from housing 12 in a proximal direction until it reaches a fully extended position corresponding to a maximum dose deliverable by device 10 in a single injection and to screw into housing 12 in a distal direction until it reaches the home or zero position corresponding to a minimum dose deliverable by device 10 in a single injection.

Figures 3, 4:
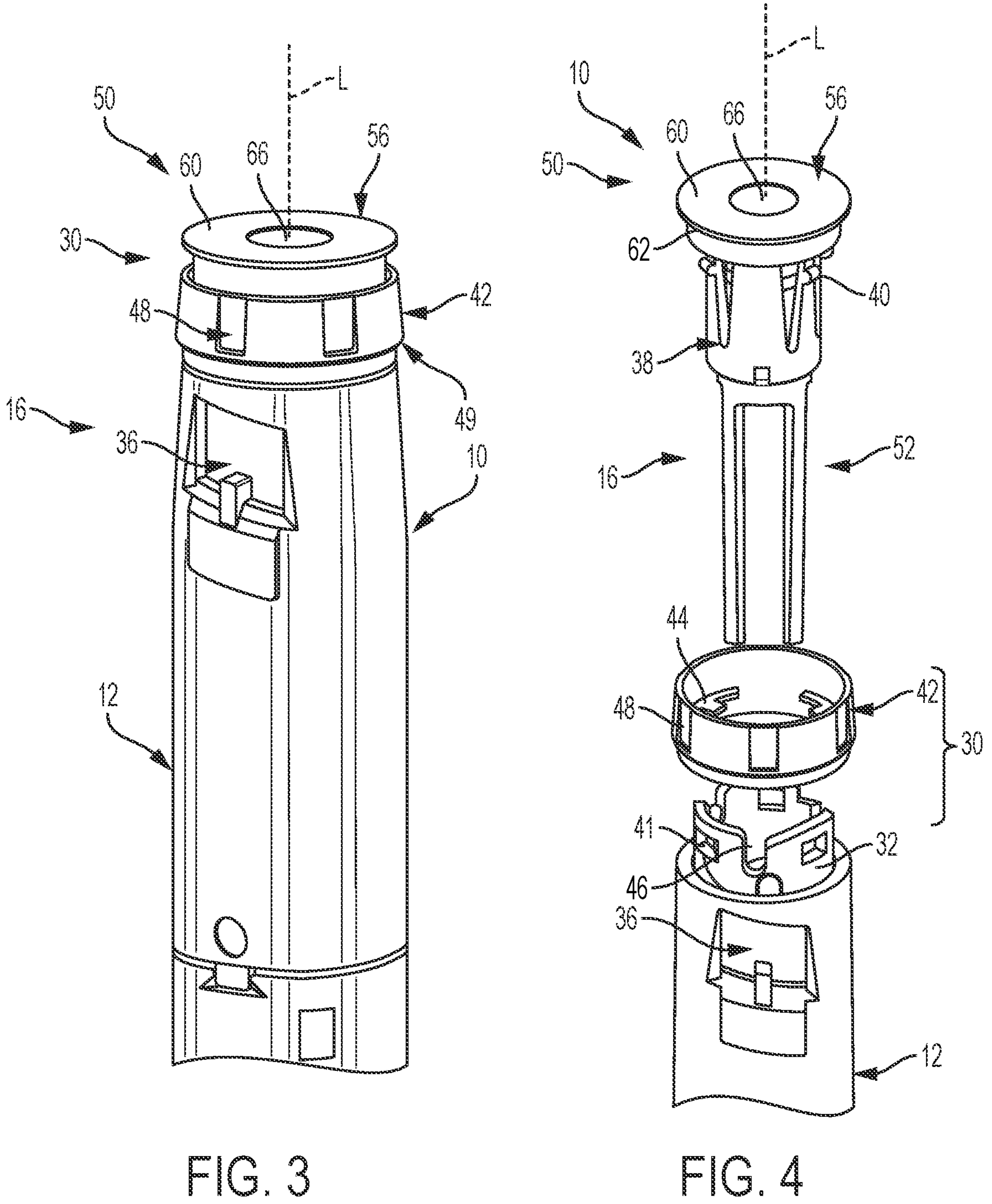
FIG. 3 is a perspective view of a proximal portion of the exemplary medication delivery device of FIG. 1.
FIG. 4 is a partially-exploded perspective view of the proximal portion of the exemplary medication delivery device of FIG. 3.

Referring to FIGS. 2-4, dose setting member 30 includes a cylindrical dial member 32 having a helically threaded outer surface 33 that engages a corresponding threaded inner surface 13 of housing 12 to allow dose setting member 30 to spiral relative to housing 12. Dial member 32 further includes a helically threaded inner surface that engages a threaded outer surface of sleeve 34 (FIG. 2) of device 10. The outer surface 33 of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotationally locked to dial member 32 by detents 40 received within openings 41 in dial member 32. Dose setting member 30 further includes a skirt or collar 42 positioned around the outer periphery of dial member 32 at its proximal end. Skirt 42 is axially and rotationally locked to dial member 32 by tabs 44 received in slots 46.

The dose setting member 30 therefore may be considered to comprise any one or all of dial member 32, flange 38, and skirt 42, as they are all rotationally and axially fixed together. The dial member 32 is directly involved in setting the dose and driving delivery of the medication. The flange 38 is attached to the dial member 32 and, as described later, cooperates with a clutch 52 to selectively couple the dial member 32 with a dose button 56. Skirt 42 provides a surface external of body 11 to rotate the dial member 32.

Skirt 42 illustratively includes a plurality of surface features 48 formed on the outer surface 49 of skirt 42. Surface features 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose button 56 and/or dial member 32 for dose setting.

Referring to FIGS. 3-4, delivery device 10 includes an actuator 50 having clutch 52 which is received within dial member 32. Clutch 52 includes an axially extending stem 54 at its proximal end, such as shown in FIG. 2. Actuator 50 further includes dose button 56 positioned proximally of skirt 42 of dose setting member 30. Dose button 56 in FIG. 2 includes a mounting collar 58 centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inwardly of the outer peripheral edge of face 60 to form an annular lip 64 there between (FIG. 2). Proximal face 60 of dose button 56 serves as a push surface against which a force can be applied manually, i.e., directly by the user to push actuator 50 in a distal direction. Dose button 56 illustratively includes a recessed portion 66 centrally located on proximal face 60 (FIGS. 3 and 4), although proximal face 60 alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation.

Delivery device 10 is operable in both a dose setting mode of operation and a dose dispensing or delivery mode of operation, as described further below.

In the dose setting mode of operation, dose setting member 30 is dialed (i.e., rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" equals one unit of medication. The set dose amount is visible to the user via the dial indicator markings shown through dosage window 36. Actuator 50, including button 56 and clutch 52, move axially and rotationally with dose setting member 30 during the dialing of the dose setting mode, because dose button 56 of actuator 50 is rotationally fixed relative to skirt 42 of dose setting member 30 by complementary and mutually-facing splines 74 (FIG. 2) urged together by bias member 68. Thus, as noted above, the user may grasp and rotate dose button 56 and/or dial member 32. In the course of the dose setting operation, skirt 42 and dose button 56 move relative to housing 12 in a spiral manner from a "start" position to an "end" position. This rotation relative to the housing 12 is proportional to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56 along longitudinal axis L. This axial distal force causes axial movement of actuator 50 in the distal direction relative to housing 12 along longitudinal axis L. The axial force may be applied by the user directly or indirectly to dose button 56, as described further below. The dose dispensing mode of operation may also be initiated by activating a separate switch or trigger mechanism.

The axial shifting motion of actuator 50 compresses biasing member 68 and reduces or closes the gap between dose button 56 and tubular flange 38. This relative axial movement separates complementary splines 74 (FIG. 2) on the clutch 52 and flange 38, and thereby disengages actuator 50 from being rotationally fixed to dose setting member 30. In particular, dose setting member 30 is rotationally uncoupled from actuator 50 to allow back-driving rotation of dose setting member 30 relative to actuator 50.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device 10 is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3.

The above-described "start" and "end" angular positions of dose dial member 32, and therefore of the rotationally fixed flange 38 and skirt 42, of the dose setting member 30 relative to dose button 56 of actuator 50 provide an "absolute" change in angular positions during the dose dispensing operation. Determining the degree of relative rotation is determined in a number of ways. By way of example, total rotation may be determined by also taking into account the incremental movements of the dose setting member 30 which measured in any number of ways by a sensing system, as described further below.

Figure 6:
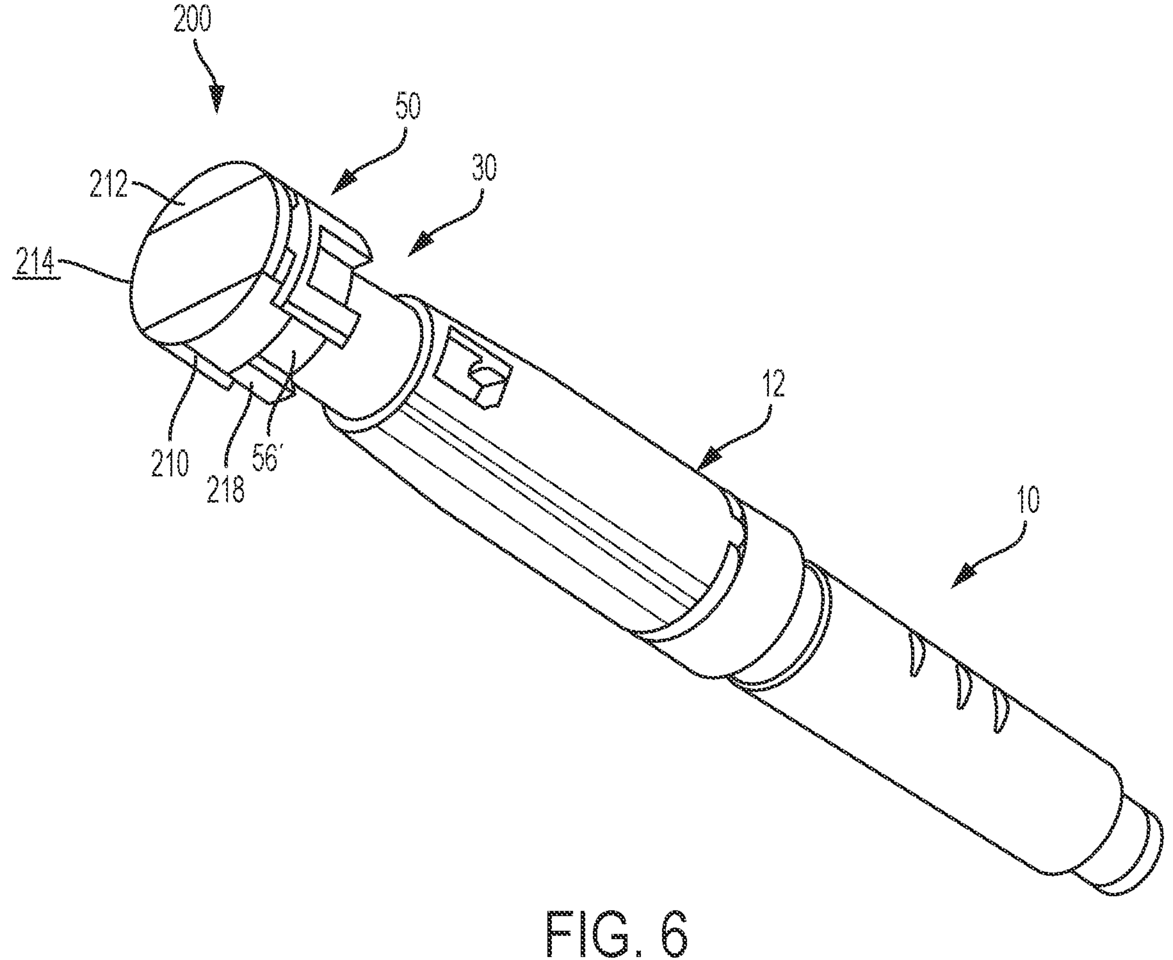
FIG. 6 is a perspective view of an exemplary modular dose detection system in combination with the exemplary medication delivery device of FIG. 1.
Figure 7:
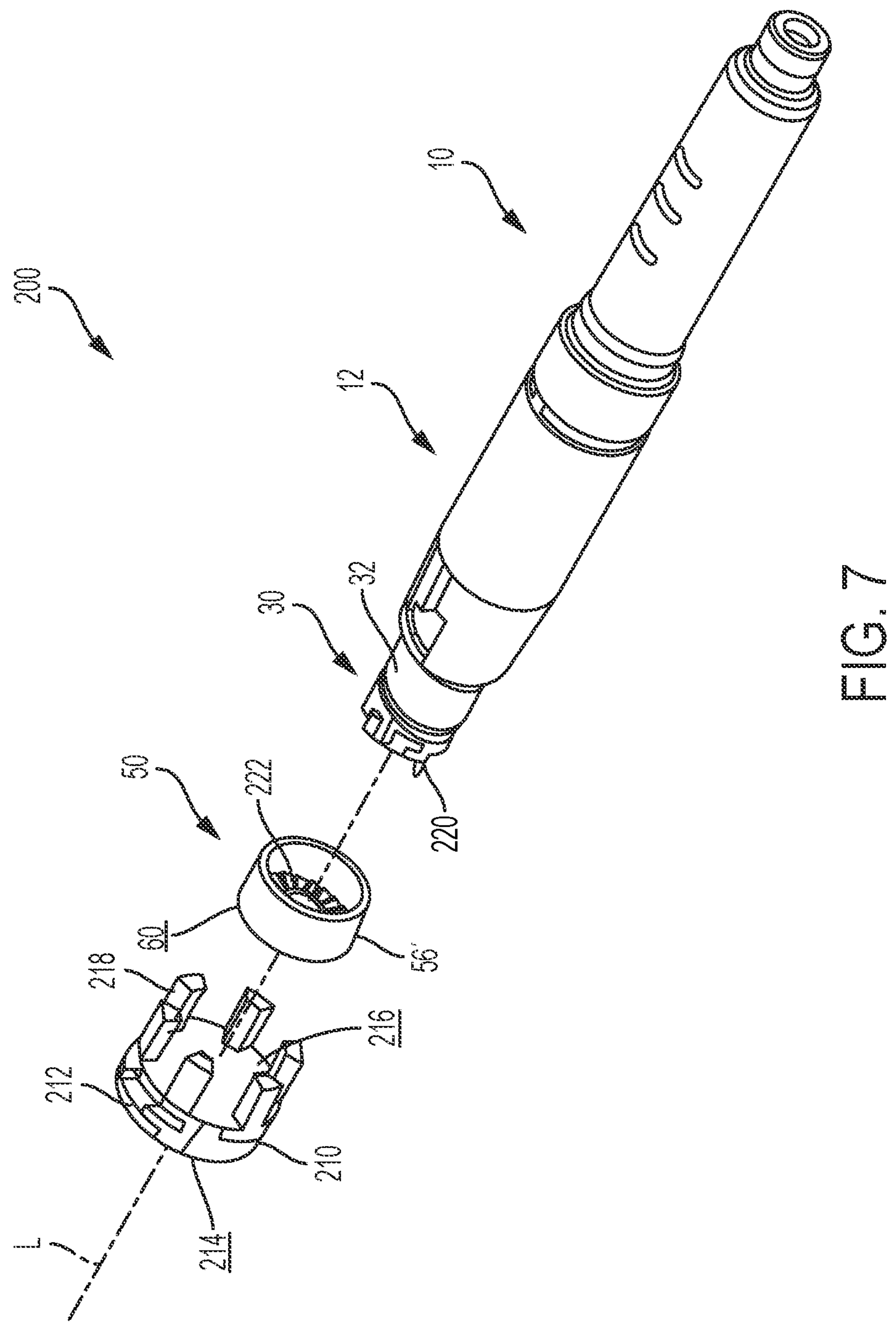
FIG. 7 is a partially-exploded perspective view of the modular dose detection system of FIG. 6.
Figure 24:
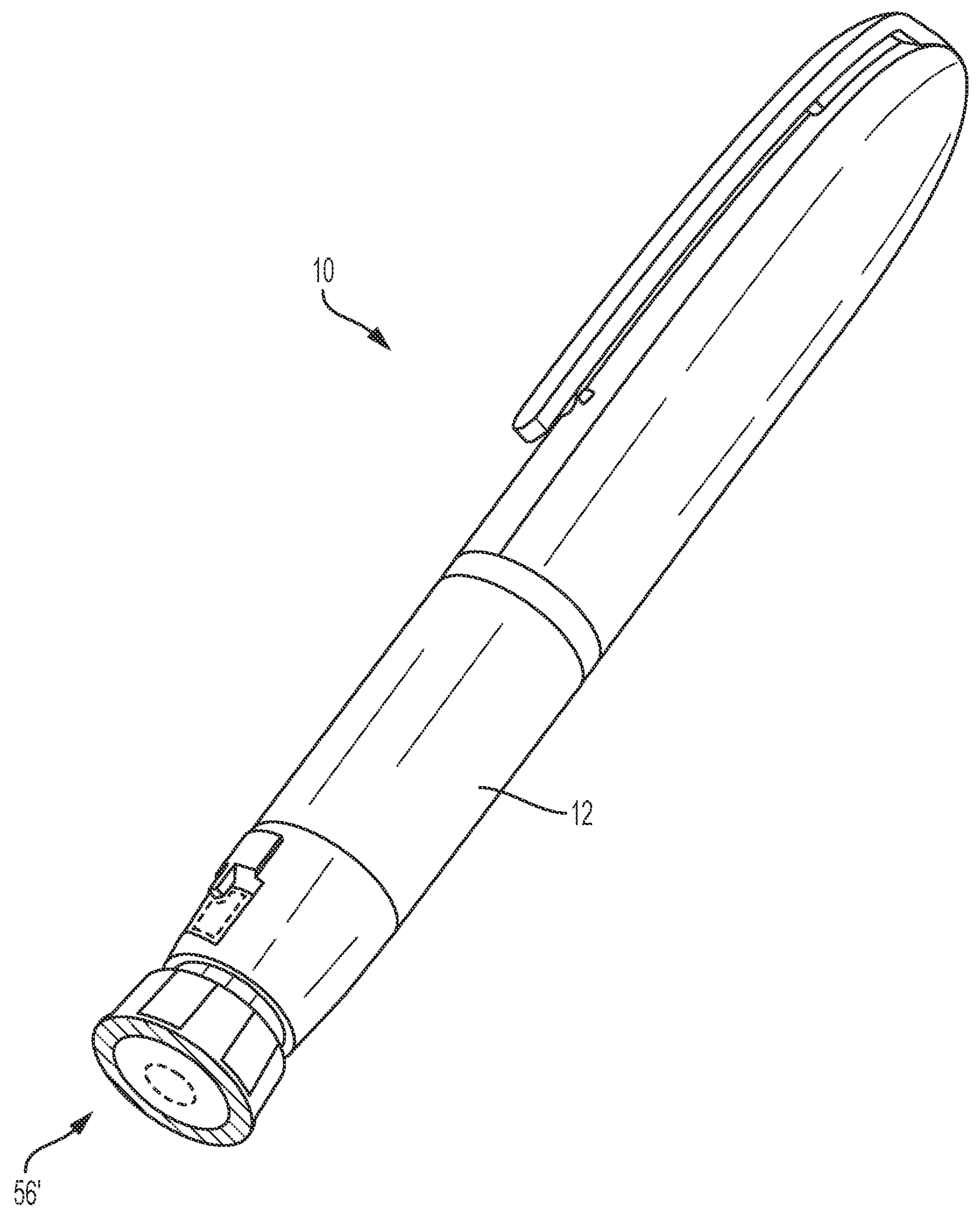
FIG. 24 is a perspective view of another exemplary medication delivery device of the present disclosure.

In other embodiments illustrated in FIG. 6-7 and 24, the actuator 50 of each dose button 56' is one piece, which combines both skirt 42 and the dose button 56 of FIGS. 1-4. In each of these embodiments, the flange 38 is attached to the dial member 32 and cooperates with clutch 52 (FIG. 4) to selectively couple the dial member 32 with the one-piece dose button 56. The radial exterior surface of each one-piece dose button 56 provides a surface external of housing 12 to rotate the dial member 32. Thus, in the embodiments of FIGS. 6-7 and 24, a user may grasp and rotate the radial exterior surface of each dose button 56 or 56', which may include a plurality of surface features, for dose setting. In the embodiments shown in FIGS. 6-7 and 24, each one-piece dose button 56' behaves substantially the same as dose button 56 of FIGS. 1-4 in the description above. One-piece component button 56' combines features of both skirt 42 and the dose button 56. In this embodiment, the flange is attached to the dial member and cooperates with a clutch, described below, to selectively couple the dial member with the one-piece dose button.

The radial exterior surface of one-piece dose button 56' provides a surface external of the device body 11 to rotate the dial member.

Further details of the design and operation of an exemplary delivery device 10 may be found in U.S. Pat. No. 7,291,132, titled "Medication Dispensing Apparatus with Triple Screw Threads for Mechanical Advantage," the entire disclosure of which is hereby incorporated by reference herein. Another example of the delivery device is an auto-injector device that may be found in U.S. Pat. No. 8,734,394, titled "Automatic Injection Device With Delay Mechanism Including Dual Functioning Biasing Member," which is hereby incorporated by reference in its entirety. Such devices may be modified with one or more various sensor systems described herein to determine an amount of medication delivered from the medication delivery device based on the sensing of relative rotation within the medication delivery device.

Various sensor systems are contemplated herein. In general, the sensor system comprises at least a pair of sensing components—a sensing component and a sensed component. The term "sensing component" refers to any component which is able to detect the relative angular position of a sensed element. The sensing component includes a sensor along with associated electrical components to operate the sensor. The "sensed element" is any component which moves relative to the associated sensor and for which the sensor is able to detect movement relative to the sensor. The sensed component comprises one or more sensed elements. Thus, the sensor is able to detect the position of the sensed element(s) and to provide outputs representative of the relative position(s) of the sensed element.

Figure 5:
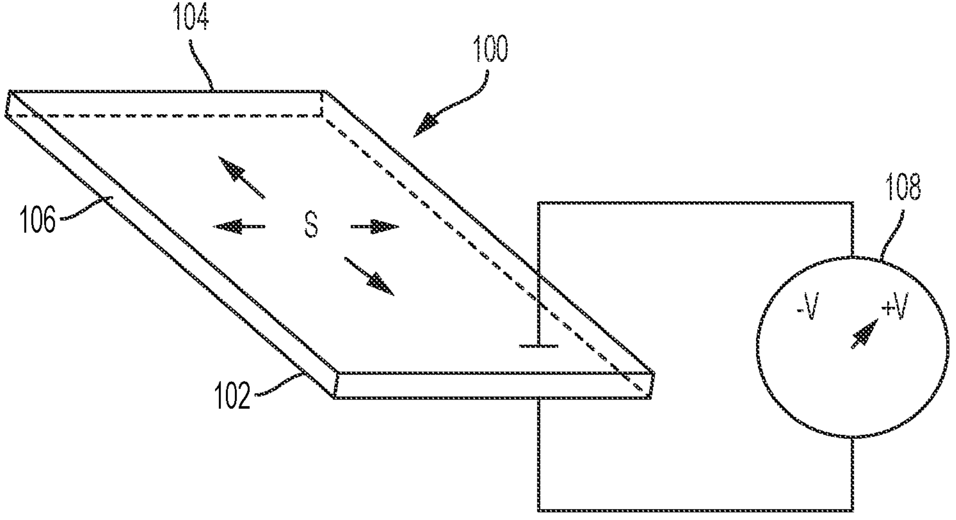
FIG. 5 is a schematic view of an exemplary piezoelectric film sensor for use with dose detection systems of the present disclosure.

Referring next to FIG. 5, an exemplary piezoelectric sensor 100 is shown in the form of a film including a first electrode 102, a second electrode 104, and a polymer core 106. Suitable polymers for use in core 106 include fluoropolymers (e.g., polyvinylidene fluoride), for example.

Piezoelectric sensor 100 is a transducer that converts mechanical energy to electrical energy. More specifically, piezoelectric sensor 100 converts mechanical deformation to a proportional electrical signal (charge or voltage). Thus, when piezoelectric sensor 100 is subjected to a mechanical force and undergoes deformation, vibration, or strain, such as stretching along one or more arrows S of FIG. 5, piezoelectric sensor 100 generates a proportional electrical signal between first electrode 102 and second electrode 104 for detection by an analog voltage detector 108. The mechanical deformation of piezoelectric sensor 100 may be elastic (i.e., reversible), such that piezoelectric sensor 100 is able to return to its original, neutral shape when the force is removed.

An exemplary piezoelectric sensor 100 is a Piezo Film Sensor available from TE Connectivity having a sensitivity of 10 to 15 mV per microstrain (ppm change in length) and a thickness of 28 μm.

Referring next to FIGS. 6-13, a dose detection system 200 is disclosed for use with medication delivery device 10 of the present disclosure or another suitable medication delivery device. Dose detection system 200 may sense rotation of dose setting member 30 relative to actuator 50 and/or another component of medication delivery device 10 during the dose dispensing operation. The sensed rotation of dose setting member 30 may be used to determine the amount of medication delivered from medication delivery device 10.

Figure 25:
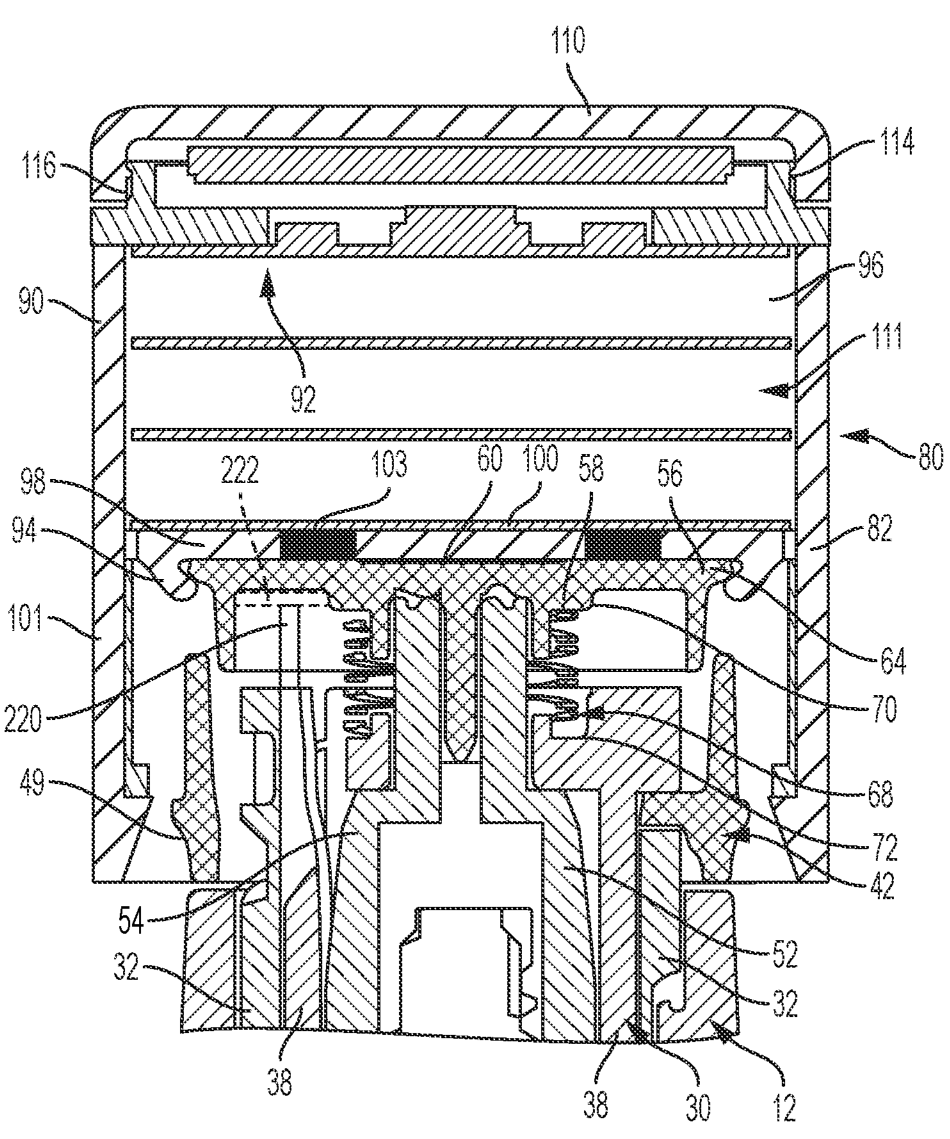
FIG. 25 is a cross-sectional view of a dose detection system according to an exemplary embodiment attached to the proximal portion of a medication delivery device.

Dose detection system 200 may be a modular component that is removably coupled to medication delivery device 10, such as, for example, shown in FIG. 25. This removable coupling allows dose detection system 200 to be removed from a first medication delivery device 10 and thereafter attached to a second medication delivery device (not shown). The removable coupling between dose detection system 200 and medication delivery device 10 is described further below.

In FIGS. 6-7, dose detection system 200 includes a frame 210 coupled to medication delivery device 10 to detect rotation of dose setting member 30, at least during the dose dispensing operation. The illustrative frame 210 is coupled to dose button 56' of actuator 50 to detect rotation of dose setting member 30 relative to actuator 50, but this location may vary. The coupling between frame 210 and dose button 56' may be axially and rotationally fixed during both the dose setting and dose dispensing operations. Frame 210 may also be rotationally coupled to dose setting member 30 during the dose setting operation, which may allow dose detection system 200 to be unaware of or ignore the combined rotation of frame 210 and dose setting member 30 during the dose setting operation. However, frame 210 may become uncoupled from dose setting member 30 during the dose dispensing operation, which may allow dose detection system 200 to detect the rotation of dose setting member 30 relative to frame 210 during the dose dispensing operation.

The illustrative frame 210 includes a proximal wall 212 having a proximal or upper surface 214 that faces the user and a distal or lower surface 216 that faces dose button 56'. Because proximal wall 212 of frame 210 may cover dose button 56', the operator may deliver a dose by applying an axial distal force along longitudinal axis L (FIG. 7) to upper surface 214 of frame 210. This axial distal force may be transferred from frame 210 to proximal face 60 of dose button 56'. The rest of the dose dispensing operation may continue as described above.

The illustrative frame 210 also includes a plurality of tabs 218 that extend distally from wall 212 to engage dose button 56' in a removable, friction fit manner. The removable coupling between frame 210 and dose button 56' may also be achieved using one or more fasteners, a threaded interface, or another suitable coupling mechanism, for example. The removable coupling between frame 210 and dose button 56' allows dose detection system 200 to be a modular component, as described further above.

Figure 8:
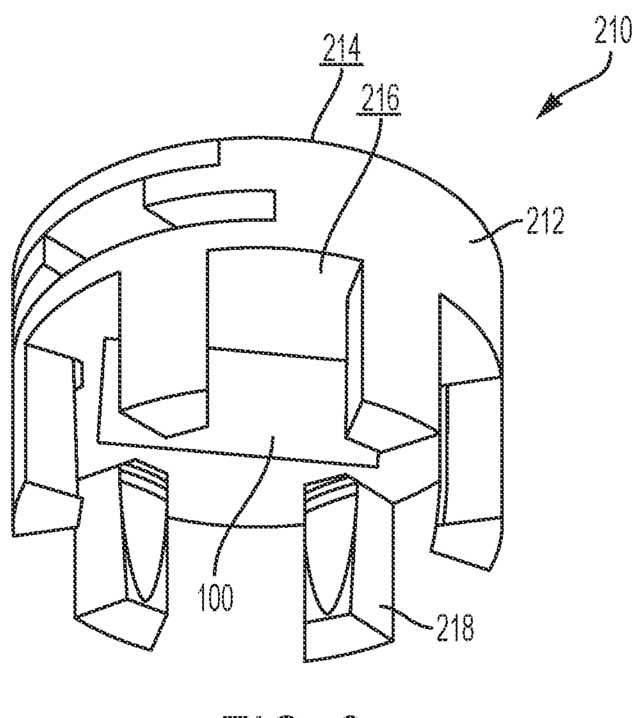
FIG. 8 is a perspective view of a frame with a piezoelectric film sensor of the modular dose detection system of FIG. 6.
Figure 9:
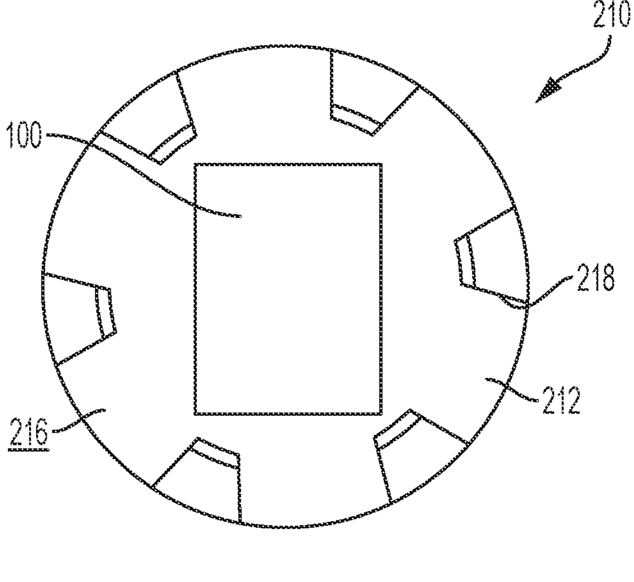
FIG. 9 is a distal plan view of the frame and the piezoelectric film sensor of FIG. 8.

As shown in FIGS. 8 and 9, frame 210 of dose detection system 200 may include at least one piezoelectric sensor 100, as described above with respect to FIG. 5. Piezoelectric sensor 100 may be adhered, bonded, or otherwise coupled to lower surface 216 of frame 210, but this location may vary. Piezoelectric sensor 100 may be coupled to frame 210 in a neutral (e.g., flat) state and configured to mechanically deform along with the adjacent dose button 56' and/or frame 210. Frame 210 of dose detection system 200 may also be configured to hold voltage detector 108 (FIG. 5) and other electronic components associated with piezoelectric sensor 100, as described further below.

As shown in FIGS. 10-13, dose detection system 200 further includes one or more rigid force applicators 220 and a plurality of deformable members 222 in mechanical communication with force applicator 220, piezoelectric sensor 100 (FIG. 8), or both, on frame 210. As dose setting member 30 rotates relative to actuator 50 during the dose dispensing operation, force applicator 220 is configured to engage and apply a mechanical force to deformable member 222. This force may be transferred from deformable member 222 to the corresponding piezoelectric sensor 100 to bend, stretch, or otherwise deform the piezoelectric sensor 100 (FIG. 8) on frame 210, as described further below. In one example, force applicator 220 resembles a finger and is coupled to the rotatable dial member 32 of dose setting member 30. In one example, deformable members 222 resemble ridges or teeth and are coupled to dose button 56' of actuator 50. The number, size, location, and orientation of force applicator 220 and deformable members 222 may vary. For example, the locations of force applicator 220 and deformable members 222 may be reversed, such that force applicator 220 would be coupled to actuator 50 and deformable members 222 would be coupled to dose setting member 30.

Figure 10:
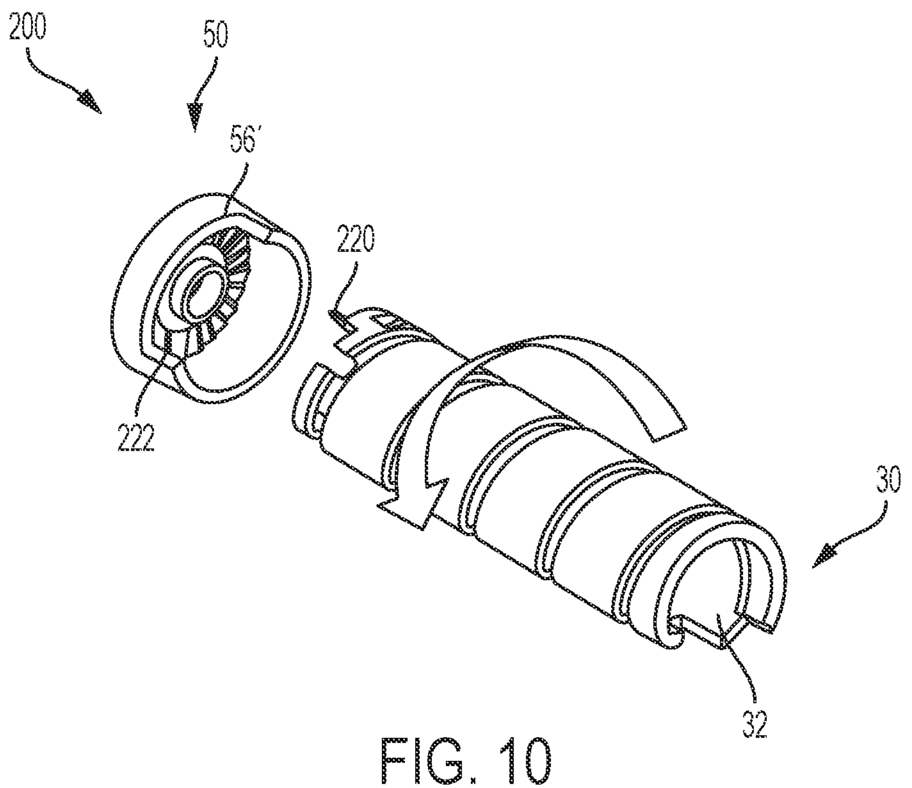
FIGS. 10 and 11 are exploded perspective views of a first embodiment of the modular dose detection system of FIG. 6, with portion of the button omitted to better illustrate the interior.
Figure 11:
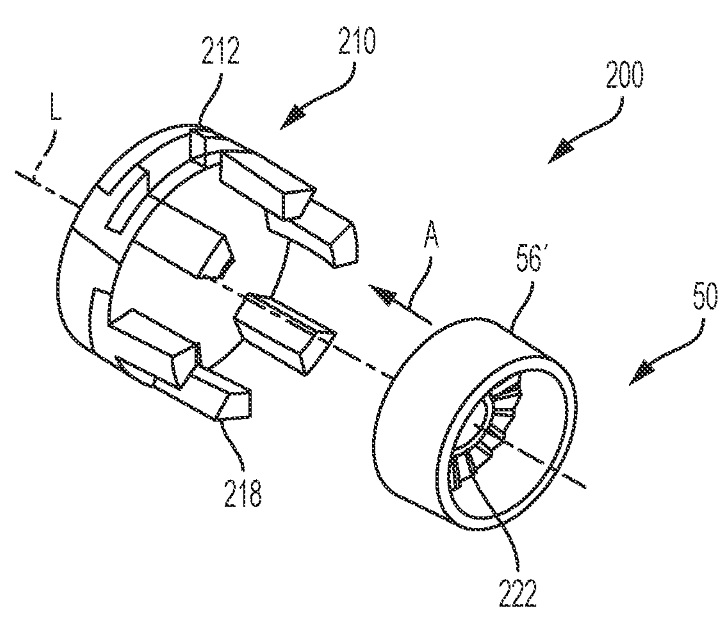

In the illustrated embodiment of FIGS. 10 and 11, force applicator 220 extends proximally from the dose member 30, shown as, for example, as the rotatable dial member 32, and deformable members 222 extend distally from dose button 56' of actuator 50. In an alternative embodiment, the one-piece dose button 56' may be replaced by the dose button 56 and skirt 42 illustrated in FIG. 3. Each time that the rigid force applicator 220 rotates across an adjacent deformable member 222, force applicator 220 applies a mechanical force to the adjacent deformable member 222 in an axial direction A that is substantially parallel to longitudinal axis L, as shown in FIG. 11. Dose button 56' of actuator 50 is flexible, so the mechanical force from force applicator 220 causes dose button 56' to deform or bend in the axial direction A. This axial deformation of dose button 56' may be transferred to piezoelectric sensor 100 (FIG. 8) on the adjacent proximal wall 212 of frame 210. The corresponding axial deformation of piezoelectric sensor 100 may occur each time that force applicator 220 rotates across an adjacent deformable member 222.

Figure 12:
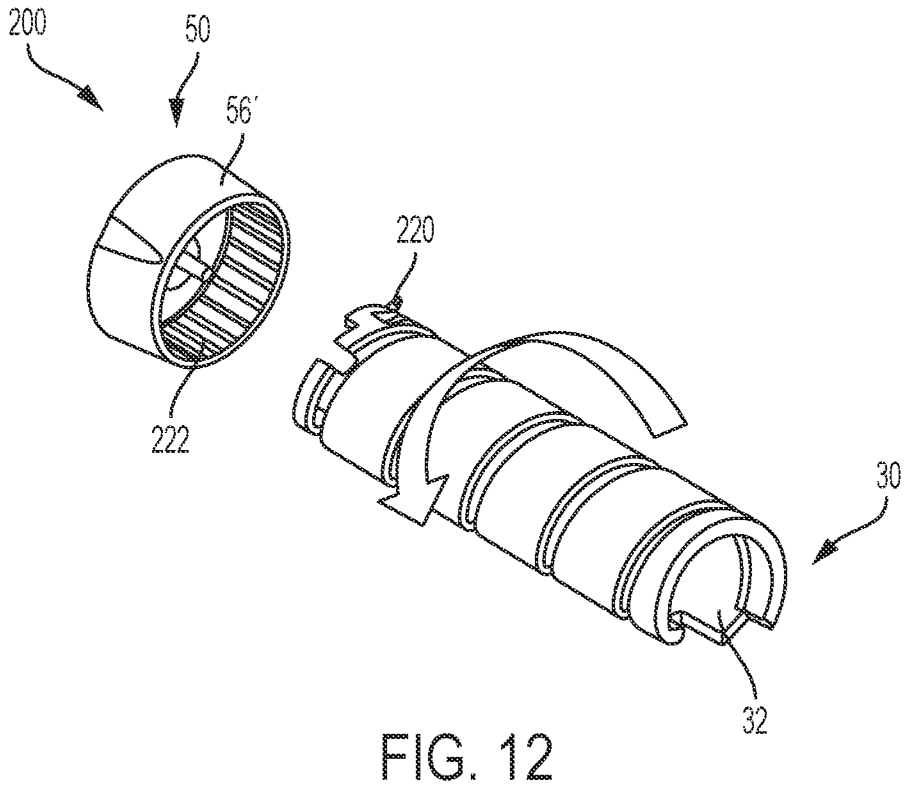
FIGS. 12 and 13 are exploded perspective views of a second embodiment of the modular dose detection system of FIG. 6.
Figure 13:
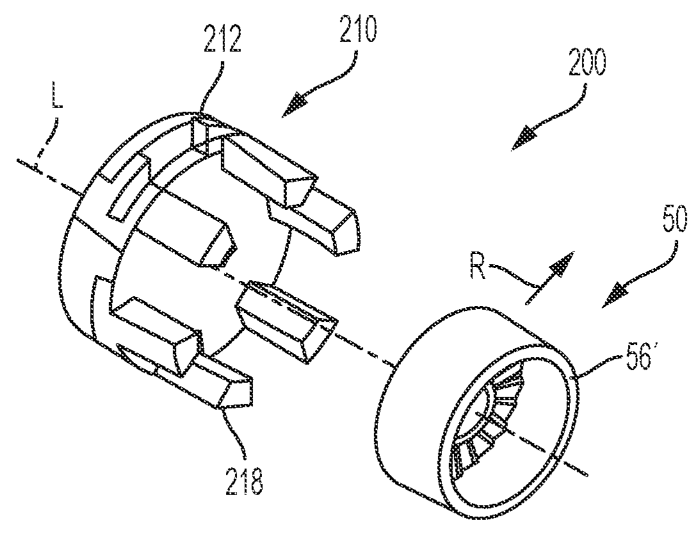

In the illustrated embodiment of FIGS. 12 and 13, force applicator 220 extends radially outward from the dose member 30, shown as the rotatable dial member 32, and deformable members 222 extend radially inward from dose button 56' of actuator 50. Each time that the rigid force applicator 220 rotates across an adjacent deformable member 222, force applicator 220 applies a mechanical force to the adjacent deformable member 222 in a radially outward direction R that is substantially perpendicular to longitudinal axis L, as shown in FIG. 13. Dose button 56' of actuator 50 is flexible, so the mechanical force from force applicator 220 causes dose button 56' to deform or bend in the radially outward direction R. This radial deformation of dose button 56' may be transferred to tabs 218 of frame 210 and then to piezoelectric sensor 100 (FIG. 8) on proximal wall 212 of frame 210. The corresponding radial deformation of piezoelectric sensor 100 may occur each time that force applicator 220 rotates across an adjacent deformable member 222. In an alternative embodiment, the one-piece dose button 56' may be replaced by the dose button 56 and skirt 42 illustrated in FIG. 3.

As described above, the sensed rotation of dose setting member 30 may be used to determine to the amount of medication delivered from medication delivery device 10. In certain embodiments, each rotation of force applicator 220 on dose setting member 30 across an adjacent deformable member 222 on actuator 50 may correlate with one dose unit. Thus, based on information received from piezoelectric sensor 100, dose detection system 200 may incrementally count the number of times force applicator 220 rotates across a deformable member 222 and correlate that number with the amount of medication delivered from medication delivery device 10. However, the size of each deformable member 222 and the distance between adjacent deformable members 222 may vary to correlate with other dose units. The dose detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable, such as, for example, 9, 10, 15, 20, 24 or 36 degrees may be used for a unit or 0.5 unit. The system is operable to determine the total angular displacement of a dose setting member during dose delivery. Thus, if the angular displacement is 90°, then 5 units of dose have been delivered. Such determined total angular displacement of the dose setting member can be correlated with an amount of dose delivered.

Dose detection system 200 could be supplied as a system that is integral to the medication delivery device 10 rather than a modular component that is removably coupled to medication delivery device 10. In this alternative embodiment, the piezoelectric sensor 100 may be coupled to the housing 12 or other component of delivery device 10 at any location that is stationary relative to dose button 56' during dose delivery and accurately detects deformation of the piezoelectric sensor 100 without excessive noise. The electronic components associated with piezoelectric sensor 100 could similarly be attached to any component of medication delivery device 10 and thus be integral to the delivery device 10.

Figure 20:
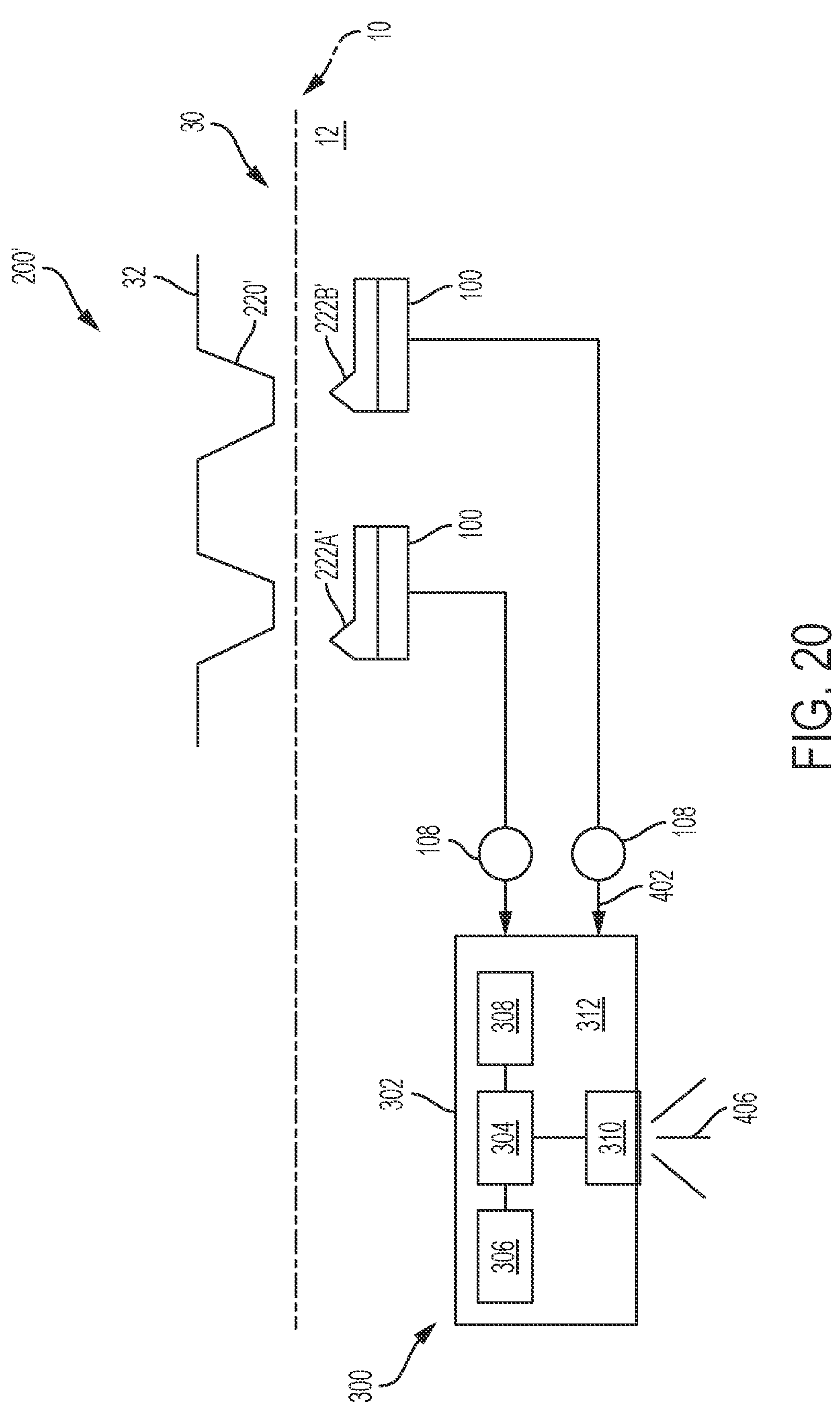
FIG. 20 is a schematic view of an exemplary electronic control system for use with the dose detection systems of the present disclosure.
Figure 22:
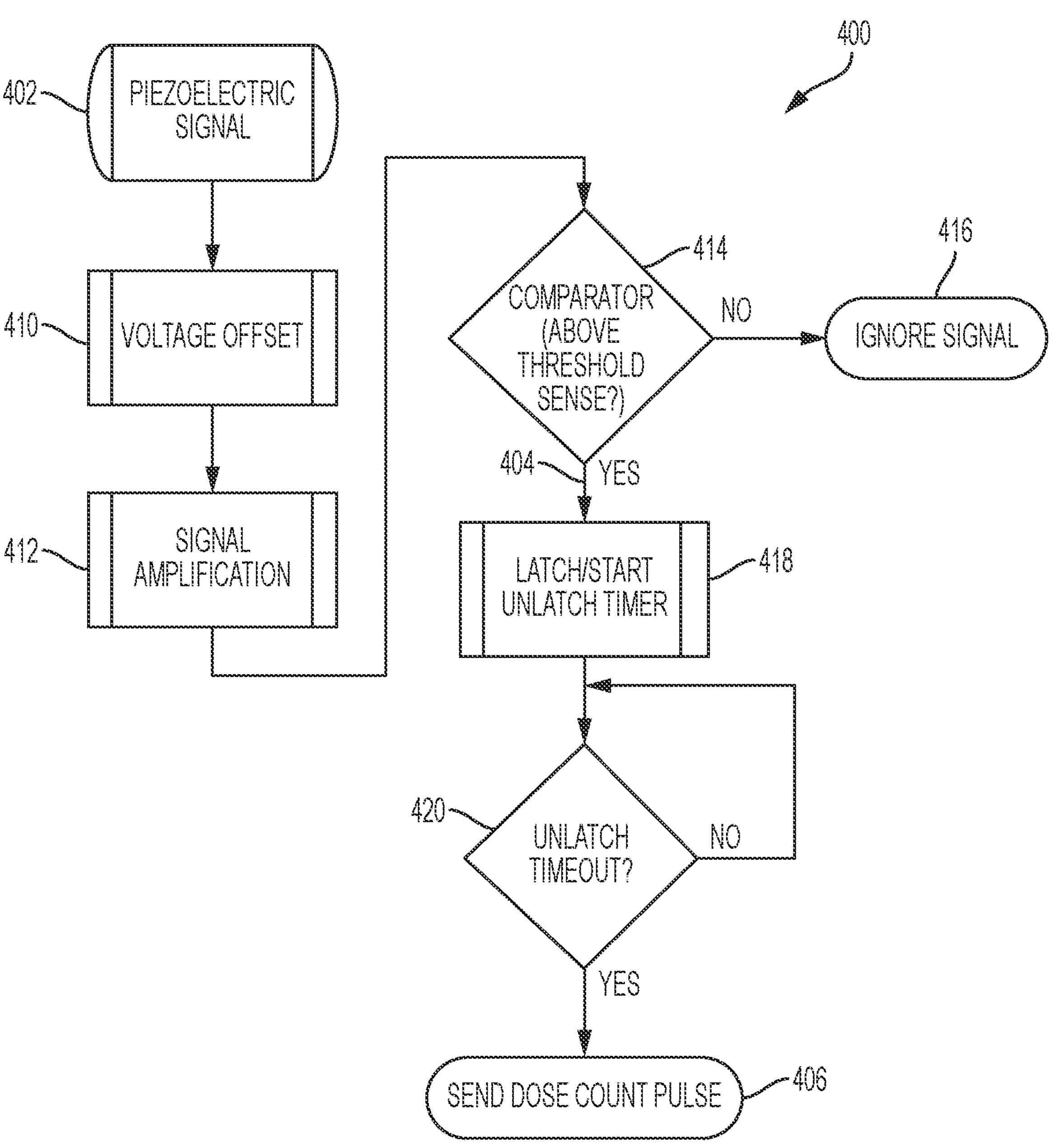
FIG. 22 is a flow chart showing a signal processing method performed by the control system of FIG. 20.

In FIG. 25, a dose delivery detection system, now referred to system 80, in the form an attachable module 82 to the button 56 of the device. The embodiments are shown in somewhat diagrammatic fashion, as common details have already been provided with respect to FIGS. 1-4. The dose detection module 82 includes a body 88 having a cylindrical upper wall 90, a top axial wall 92, and a lower axial wall 98, although it will be appreciated that variations on these components, including the absence of lower wall 98, are within the scope of the disclosure. Other parts common to the earlier descriptions herein include an electronics assembly 111 contained within a cavity 96 of module body 88, dose button 56, dose setting member 32 and device housing 12. Electronics assembly 111 may include electronic components, such as depicted in FIGS. 20 and 22, including the controller. Further, the dose detection module 82 is diagrammatically shown as being attached to the annular side wall 62 of dose button 56, although alternative forms and locations of attachment may be used. For example, dose detection module 82 may be attached to dose button 56 and releasably attached to skirt 42 in some embodiments. Also, dose detection module 82 may be attached to one-piece dose button 56' as can be appreciated by those skilled in the art. Attached to top wall 92 of module 82 is a finger pad 110. Finger pad 110 is coupled to top wall 92, which is in turn attached to upper side wall 90. Finger pad 110 includes a ridge 114 which extends radially inward and is received within circumferential groove 116 of wall component 92. Groove 116 allows a slight axial movement between finger pad 110 and wall component 92. Springs (not shown) normally urge finger pad 110 upwardly away from wall component 92. Finger pad 110 may be rotationally fixed to wall component 92. Axial movement of finger pad 110 in the distal direction toward module body 88 as the injection process is initiated may be used to trigger selected events. One use of finger pad 110 may be the activation of the medication delivery device electronics upon initial pressing and axial movement of the finger pad 110 relative to the module body 88 when dose injection is initiated. For example, this initial axial movement may be used to “wake up” the device, and particularly the components associated with the dose detection system.

In the absence of a finger pad, the system electronics may be activated in various other ways. For example, the initial axial movement of module 82 at the start of dose delivery may be directly detected, such as by the closing of contacts or the physical engagement of a switch. It is also known to activate a medication delivery device based on various other actions, e.g., removal of the pen cap, detection of pen movement using an accelerometer, or the setting of the dose. In many approaches, the dose detection system is activated prior to the start of dose delivery.

Dose detection module body 88 is removably attachable to dose button 56 or 56'. By way of example, in FIG. 25 upper side wall 90 is diagrammatically shown having inwardly-extending tabs 94 configured for attaching module 82 to dose button 56. Lower wall 101 of body 88 may include attachment features for a more distal location. Dose detection module 82 may alternatively be attached to dose button 56 or 56' via any suitable fastening means, such as a snap or press fit, threaded interface, etc., provided that in one aspect module 82 may be removed from a first medication delivery device and thereafter attached to a second medication delivery device. The attachment may be at any location on dose button 56 or 56', provided that dose button 56 or 56' is able to move any required amount axially relative to dose setting member 30, as discussed herein.

During dose delivery, dose setting member 30 is free to rotate relative to dose button 56 or 56' and module 82. In the illustrative embodiment, module 82 is rotationally fixed with dose button 56 and does not rotate during dose delivery. This may be provided structurally, such as with tabs 94, or by having mutually-facing splines or other surface features on the module body 88 and dose button 56 engage upon axial movement of module 82 relative to dose button 56. In another embodiment, the distal pressing of the module provides a sufficient frictional engagement between module 82 and dose button 56 as to functionally cause the module 82 and dose button 56 to remain rotationally fixed together during dose delivery. In FIG. 25, piezoelectric sensor 100 is shown disposed within cavity 96 along proximal surface of lower wall 98. One or more openings 103 defined by the lower wall 98 may be included to permit direct sensing for the sensor 100 along proximal face 60 of the button 56. With additional reference to FIG. 7, the distal face, opposite the proximal face 60, of the button 56 includes the deformable member 222 (in dashed lines). The force applicator 220 is shown extending from the dose setting member 30, shown here as the flange 38 although it can be the dose dial member 32, to contact the members 222. Sensor 100 can detect relative rotational movement between the force applicator 220 and the deformable members 222. Detection may be further enhanced by portions of the sensor 100 residing within the opening(s) 103 and in engagement with proximal face 60 of the button.

Referring next to FIGS. 14-19, another dose detection system 200' is disclosed for use with medication delivery device 10 of the present disclosure or another suitable medication delivery device. Dose detection system 200' may sense rotation of dose setting member 30 relative to housing 12 and/or another component of medication delivery device 10 during the dose dispensing operation. The sensed rotation of dose setting member 30 may be used to determine the amount of medication delivered from medication delivery device 10. The second dose detection system 200' of FIGS. 14-19 is similar to the first dose detection system 200 of FIGS. 6-13, with like reference numerals indicating like elements, except as described below.

The second dose detection system 200' of FIGS. 14-19 may be an integral component that is permanently coupled to medication delivery device 10. This integral coupling eliminates the need to remove and transfer dose detection system 200' from a first medication delivery device 10 to a second medication delivery device (not shown). Rather, dose detection system 200' would be supplied as an integral part of each medication delivery device 10.

Figure 14:
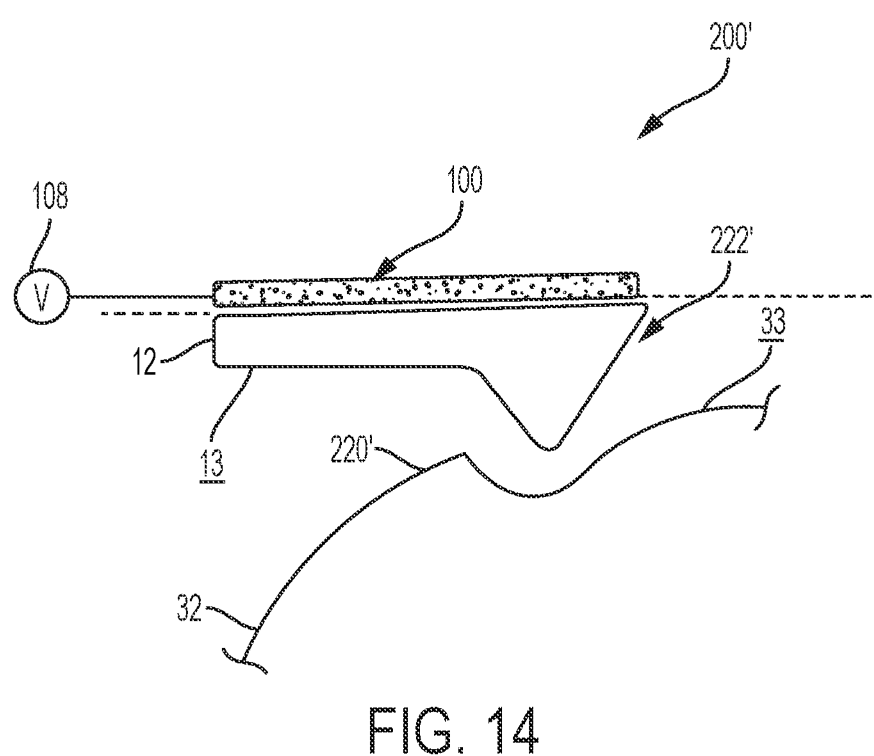
FIG. 14 is a schematic axial view of an exemplary dose detection system that is integral with a medication delivery device, wherein the dose detection system is shown in a neutral state.
Figure 15:
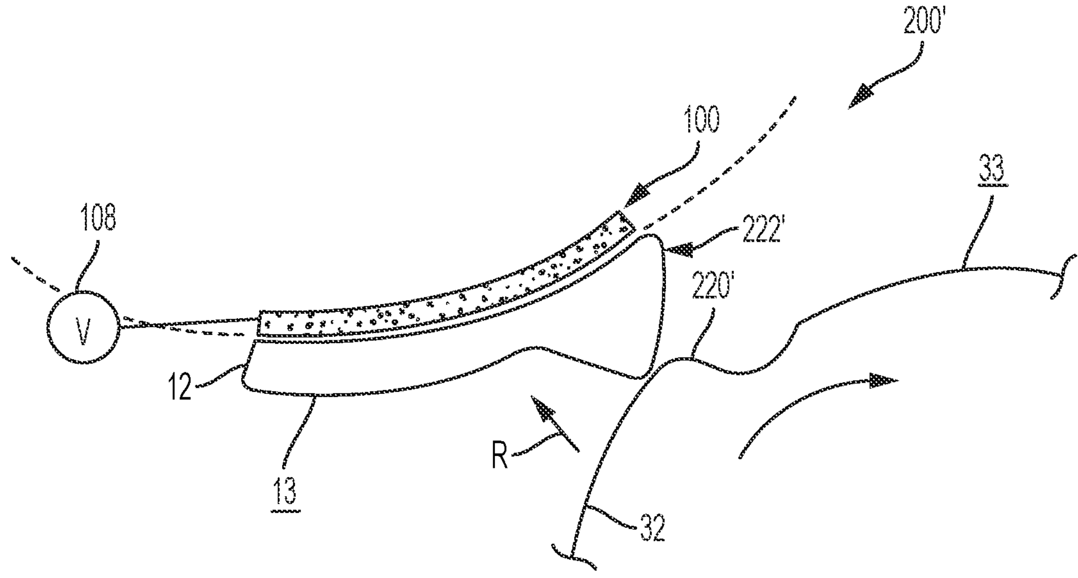
FIG. 15 is another schematic axial view similar to FIG. 14, wherein the dose detection system is shown in a deformed state.

Dose detection system 200' includes a plurality of rigid force applicators 220' and one or more deformable members 222' in mechanical communication with force applicators 220' and piezoelectric sensor 100, as shown in FIGS. 14 and 15. Force applicators 220' resemble buttons or gear teeth and are coupled to outer surface 33 of the rotatable dial member 32 of dose setting member 30. Deformable members 222' resemble arms or teeth and are coupled to inner surface 13 of the surrounding housing 12. The number, size, location, and orientation of force applicators 220' and deformable members 222' may vary. For example, the locations of force applicators 220' and deformable members 222' may be reversed, such that force applicators 220' would be coupled to housing 12 and deformable members 222' would be coupled to dose setting member 30. As dose setting member 30 rotates relative to housing 12 during the dose dispensing operation, each force applicator 220' is configured to engage and apply a mechanical force to an adjacent deformable member 222'. This force may be transferred from deformable member 222' to the corresponding piezoelectric sensor 100 to bend, stretch, or otherwise deform the piezoelectric sensor 100, as described further below.

As described above, piezoelectric sensor 100 may be arranged in mechanical communication with each deformable member 222' on housing 12. More specifically, piezoelectric sensor 100 may be adhered, bonded, or otherwise coupled to each deformable member 222' on housing 12, but this location may vary. Piezoelectric sensor 100 may be coupled to deformable member 222' in a neutral (e.g., flat) state, as shown in FIG. 14, and configured to mechanically deform along with deformable member 222' when deformable member 222' engages an adjacent force applicator 220', as shown in FIG. 15. Housing 12 may also be configured to hold voltage detector 108 (FIG. 5) and other electronic components associated with piezoelectric sensor 100, as described further below.

Figures 16, 17:
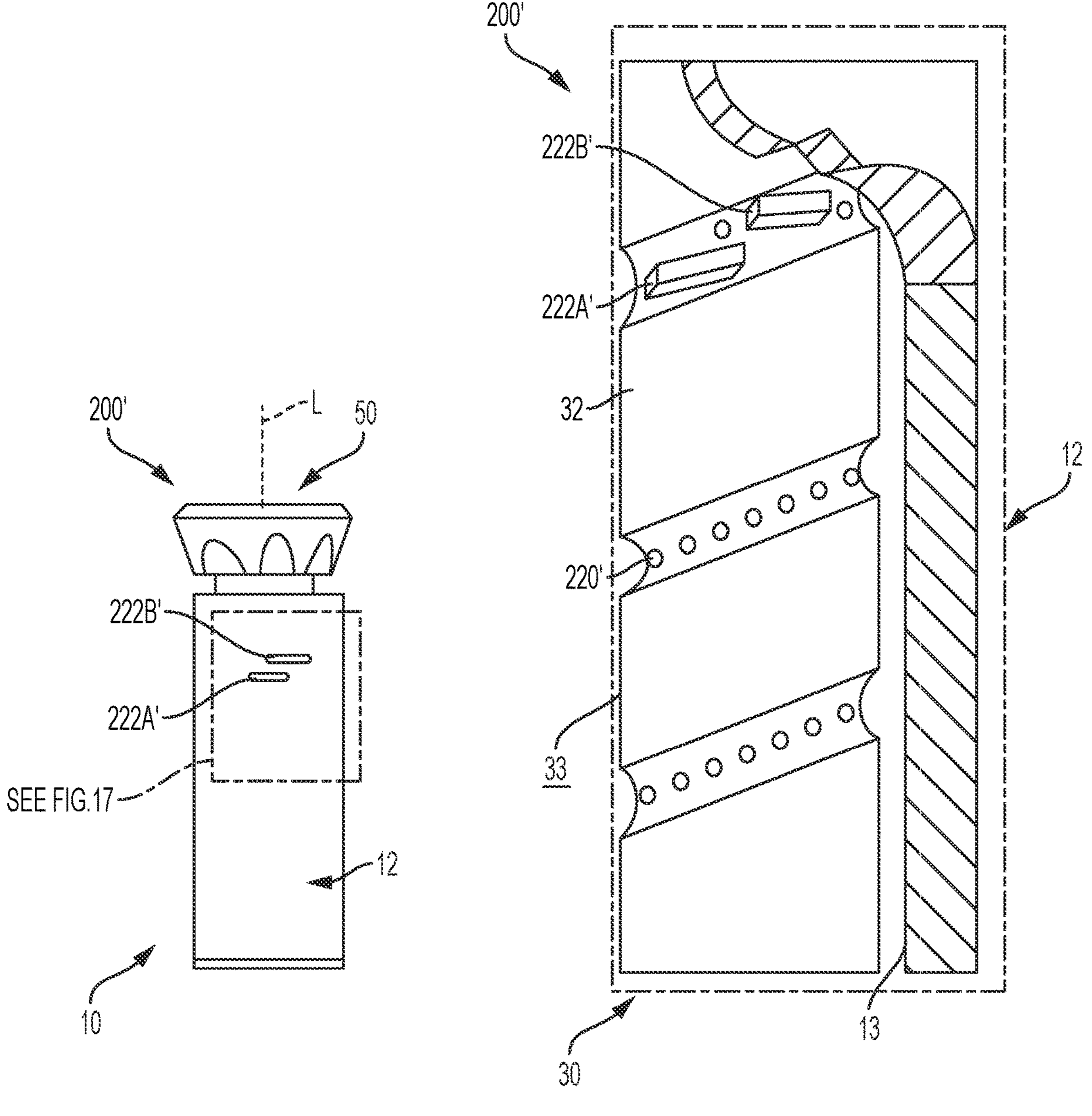
FIG. 16 is a partial elevational view of a first embodiment of an exemplary dose detection system that is integral with a medication delivery device.
FIG. 17 is a detailed view of the area identified in FIG. 16 with a portion of the housing removed.

In the illustrated embodiment of FIGS. 16 and 17, two deformable members 222A'-222B' extend radially inward from inner surface 13 of housing 12, each in mechanical communication with a corresponding piezoelectric sensor 100 (FIG. 14). Force applicators 220' extend radially outward from outer surface 33 of dial member 32 and are arranged in a helical pattern that follows the threaded pathway on outer surface 33 of dial member 32. Each time that one of the deformable members 222A'-222B' rotates across an adjacent force applicator 220', the force applicator 220' applies a mechanical force in a radially outward direction R (FIG. 15) that is substantially perpendicular to longitudinal axis L (FIG. 16). Deformable members 222A'-222B' may be flexible, so the mechanical force from force applicator 220' causes the adjacent deformable member 222A'-222B' and its corresponding piezoelectric sensor 100 to deform or bend in the radially outward direction R. The radial deformation of piezoelectric sensor 100 may be correlated with the amount of medication delivered from medication delivery device 10.

Figures 18, 19:
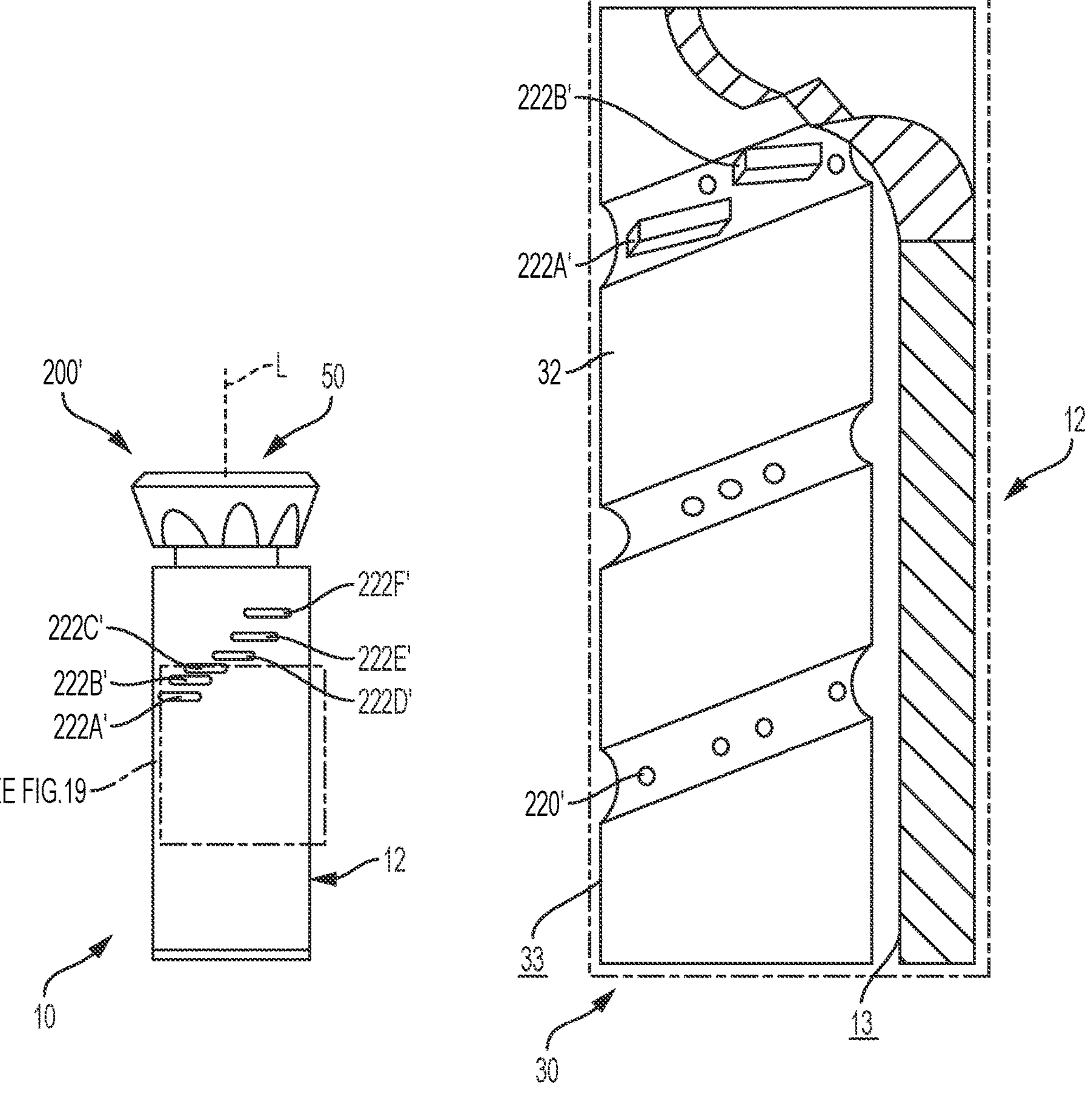
FIG. 18 is a partial elevational view of a second embodiment of an exemplary dose detection system that is integral with a medication delivery device.
FIG. 19 is a detailed view of the area identified in FIG. 18 with a portion of the housing removed.

In the illustrated embodiment of FIGS. 18 and 19, six deformable members 222A'-222F' extend radially inward from inner surface 13 of housing 12, each in mechanical communication with a corresponding piezoelectric sensor 100 (FIG. 14). Force applicators 220' extend radially outward from outer surface 33 of dial member 32 and are arranged in a helical pattern that follows the threaded pathway on outer surface 33 of dial member 32. Each time that one of the deformable members 222A'-222F' rotates across an adjacent force applicator 220', the force applicator 220' applies a mechanical force in a radially outward direction R (FIG. 15) that is substantially perpendicular to longitudinal axis L (FIG. 18). Deformable members 222A'-222F' may be flexible, so the mechanical force from force applicator 220' causes the adjacent deformable member 222A'-222F' and its corresponding piezoelectric sensor 100 to deform or bend in the radially outward direction R. The radial deformation of piezoelectric sensor 100 may be correlated with the amount of medication delivered from medication delivery device 10.

Figure 26:
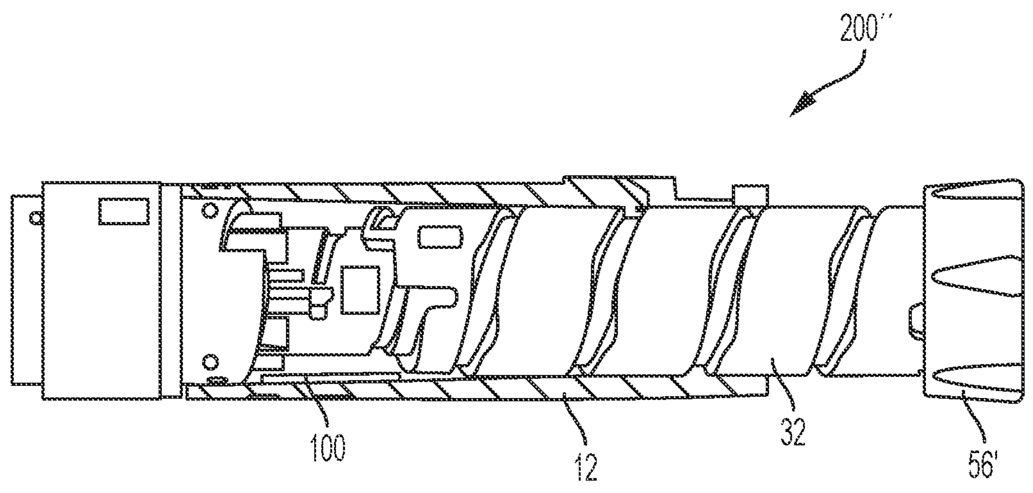
FIG. 26 is a cut-away side view of another exemplary medication delivery device of the present disclosure.

An additional embodiment of dose detection system 200" is shown in FIG. 26 for use with medication delivery device 10 of the present disclosure or another suitable medication delivery device. The illustrative device 10 includes housing 12, dial member 32, and dose button 56', which are described further above. Dose detection system 200" only requires a single piezoelectric strain sensor 100 measuring deformation on the housing 12. This sensor 100 could measure strain on the housing 12 during dosing where strain is the result of a direct mechanical deformation or a transmission of an indirect mechanical wave. A mechanical wave can be generated, as shown for example in FIG. 10, by the rhythmic movement of force applicator 220 as it interacts with successive adjacent deformable members 222 during relative rotation of dose button 56' to rotatable dial member 32. Like the previous embodiments, the signal from the piezoelectric sensor 100 may be used to determine the amount of medication delivered from medication delivery device 10.

Figure 27:
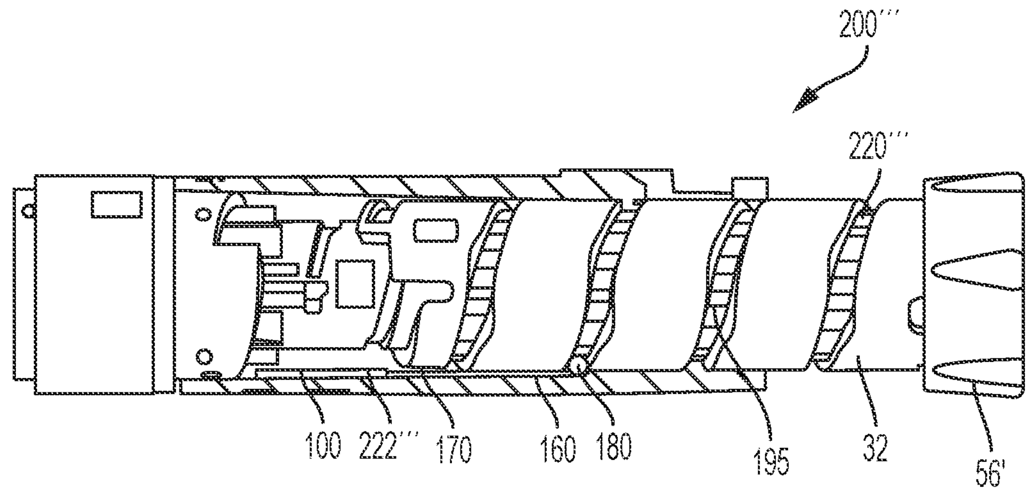
FIG. 27 is a cut-away side view of another exemplary medication delivery device of the present disclosure.
Figures 28, 29:
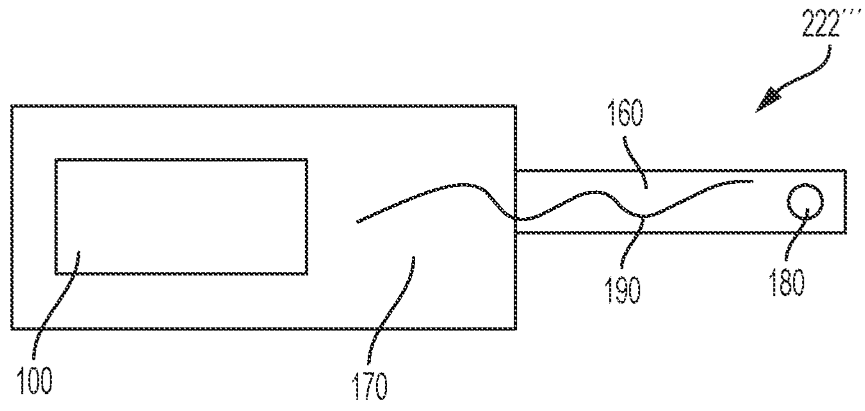
FIG. 28 is a representative view of a frame that the piezoelectric strain sensor may be mounted on in one exemplary embodiment of the present disclosure.
FIG. 29 is a representative view of the interaction of a ball spring reader and divots or depressions on the dose dial member.

A further embodiment of dose detection system 200'" is shown in FIGS. 27-29 for use with medication delivery device 10 of the present disclosure or another suitable medication delivery device. The illustrative device includes housing 12, dial member 32, and dose button 56', which are described further above. The dose dial member 32 includes force applicators 220'" in the form of raised areas between divots or depressions 195, such that a strain is generated through a deformable member 222'" that the sensor 100 is adhered to. In the embodiment of FIG. 27, the piezoelectric strain sensor 100 may be mounted on the deformable member 222'" including a frame 170 (FIG. 28) with a ball spring arm 160 that positions a "reader" ball spring 180 to ride the divots or depressions 195 between the force applicators 220'" in the dose dial member 32 as it rotates. Piezoelectric strain sensor 100 experiences deformation as ball spring arm 160 conducts strain transmission 190 through the framework 170 from the movement of ball spring reader 180 over the divots or depressions 195 between the force applicators 220'" in the dose dial member 32.

FIGS. 28 and 29 show the relationship between the ball spring reader 180, attached to ball spring arm 160, and divots or depressions 195 on the dose dial member 32. This embodiment has an advantage in that the smooth wave of movement sensed by the ball spring reader 180 minimizes drag on glide force for injection. Like the previous embodiments, the signal from the piezoelectric sensor 100 may be used to determine the amount of medication delivered from medication delivery device 10. In an embodiment with a single piezoelectric sensor 100, the signal from the piezoelectric sensor 100 may need to be combined with a second signal to indicate that a dose is being delivered in order for the system to detect the amount of medication delivered from medication delivery device 10. A signal to indicate that a dose is being delivered could include, for example, a signal that the dose button 56' is depressed or that there is an increased strain on the lead screw 28 that is pushing the piston 26 and medication out of the device 10.

Figure 30:
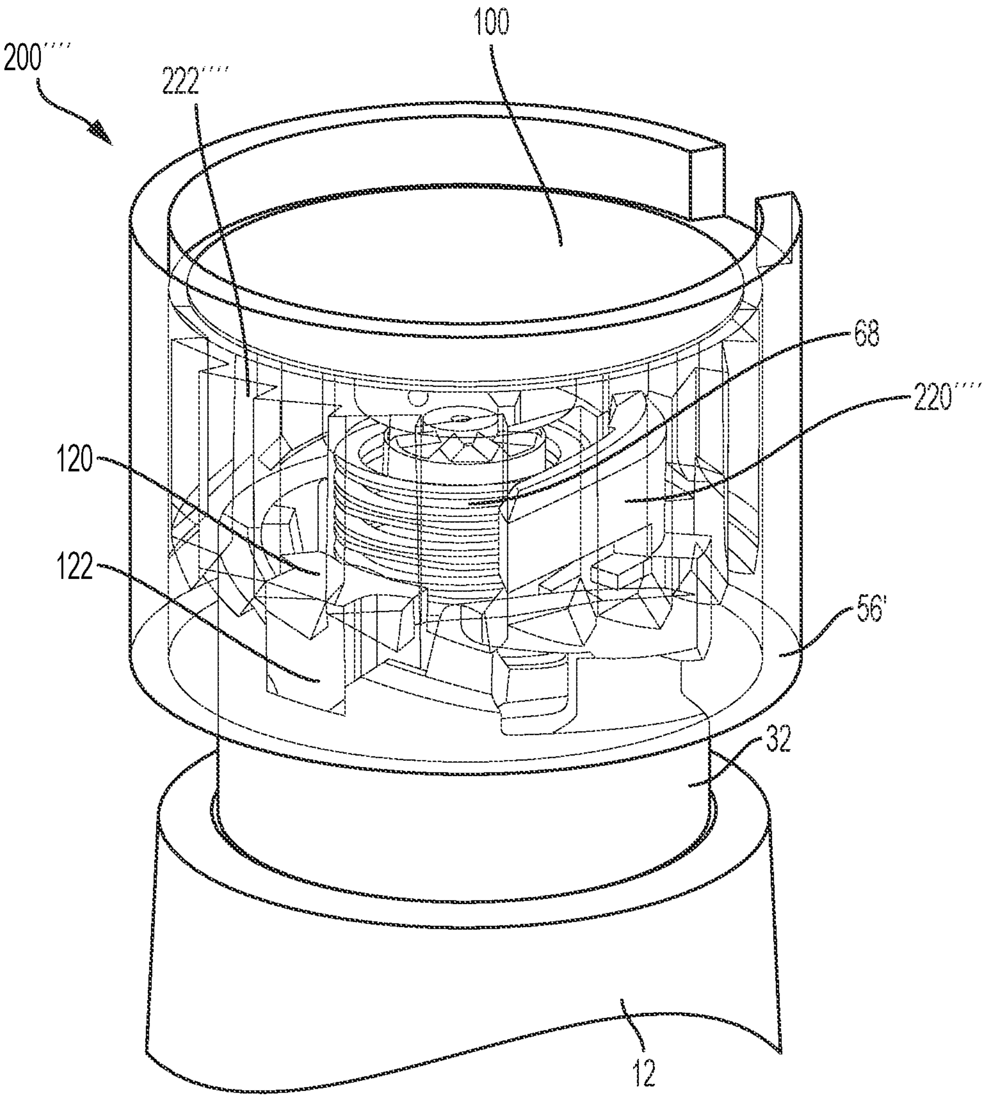
FIG. 30 is an assembled perspective view of another medication delivery device of the present disclosure including a ratchet-based, piezoelectric dose detection system.
Figure 31:
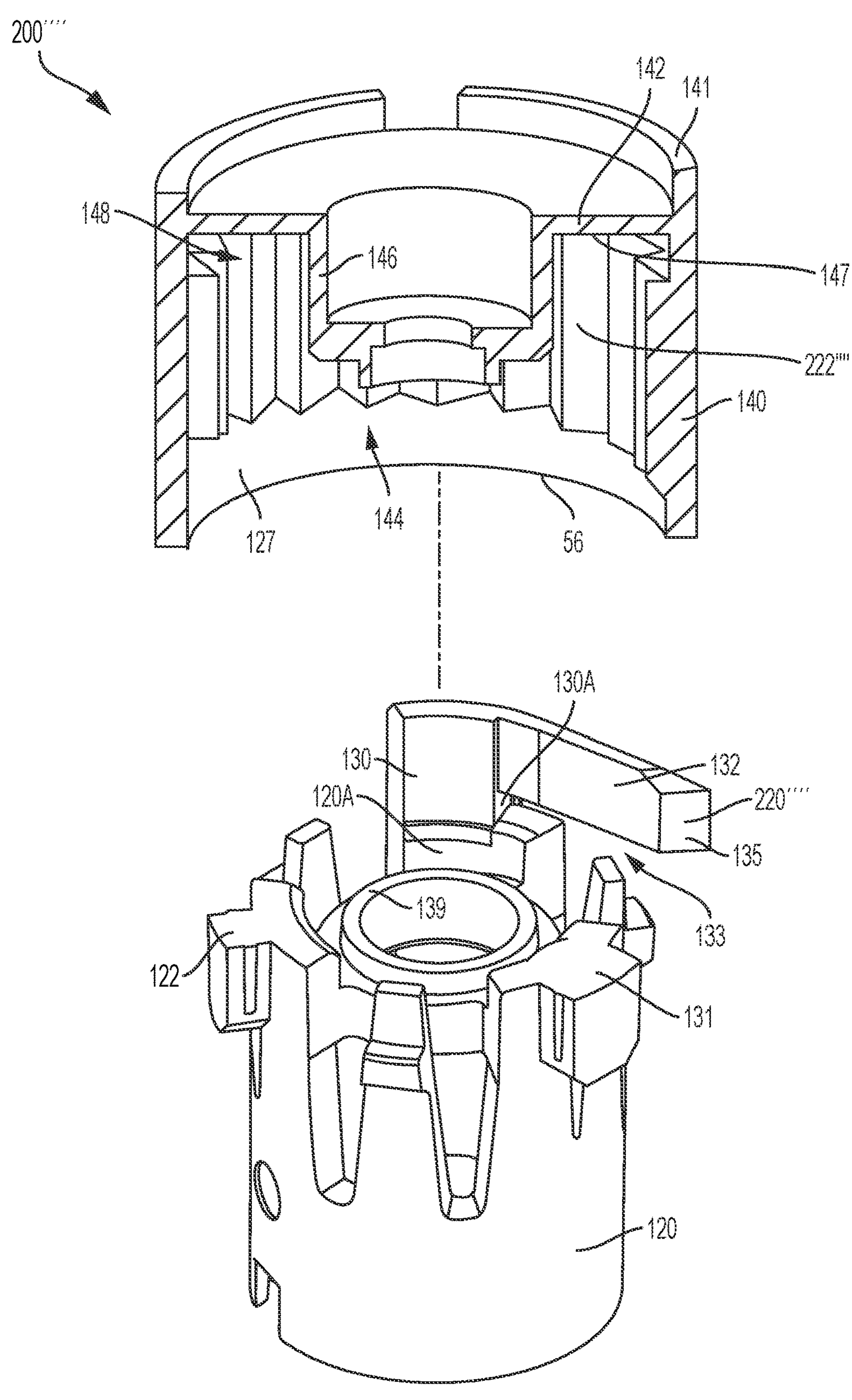
FIG. 31 is an exploded perspective view of the dose detection system of FIG. 30.
Figure 32:
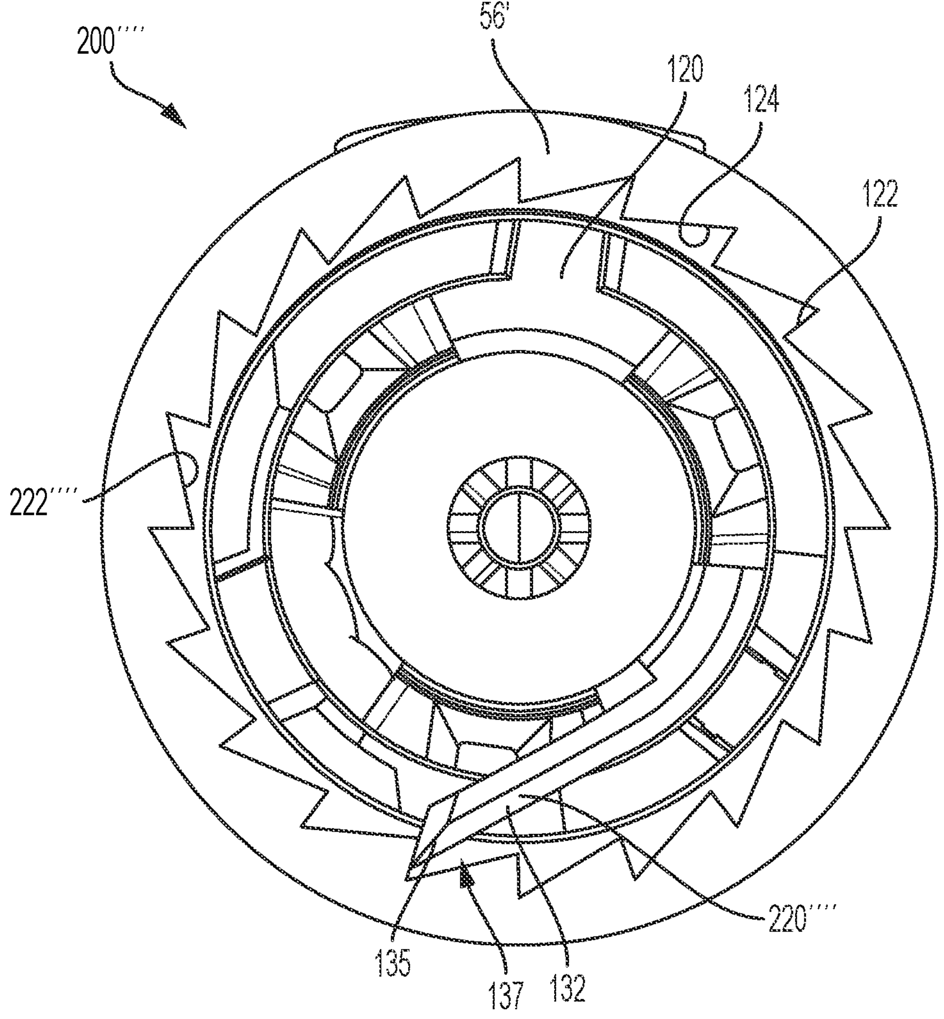
FIG. 32 is a cross-sectional view of the dose detection system of FIG. 30.

A further embodiment of dose detection system 200"" is shown in FIGS. 30-32 for use with medication delivery device 10 of the present disclosure or another suitable medication delivery device. The illustrative device includes housing 12, dial member 32, and dose button 56', which are described further above. The flange, referred to now as flange 120, is positioned between dial member 32 and dose button 56'. Dose button 56' is shown without a top plate in order to better illustrate the location of the sensor 100. Flange 120 is axially and rotatably fixed together with dial member 32. In one example, flange 120 includes a plurality of protrusions 122 configured for receipt in recesses or openings formed in the dial member 32 so as to axially and rotatably fix together flange 120 and dial member 32.

Dose detection system 200"" includes a plurality of deformable members 222"" in the form of ratchet gear teeth that extend radially inward from an interior wall of dose button 56' and the force applicator 222"" in the form of a ratchet pawl that extends radially outward from the dose setting member, show as the flange 120. Each of the gear teeth of deformable member 222"" may extend longitudinally along the inner wall 127 of the dose button 56'. Gear teeth include a first lateral side 123 that is contacted by the force applicator 220"" in a clockwise direction and a second lateral side 124 that is contacted by the force applicator in a counter-clockwise direction, or vice versa. In one example, the first lateral side 123 has a flat side configuration to inhibit movement of the force applicator 220"" in the respective direction, and the second lateral side has a sloped side configuration to aid in movement of the force applicator 220"" in the opposite direction. Dose detection system 200"" further includes the piezoelectric sensor 100 supported by dose button 56' as shown in FIG. 30. The location of the sensor is shown in a proximal location and contained by the button; however, the location of sensor 100 may vary.

Force applicator 220"" may include a base 130 and a finger portion 132 extending from the base 130. The base 130 may be extended proximally from the wall 120A of the flange 120, as shown in FIG. 31. In other embodiments, the base 130 may be mounted to another dose setting member component, such as, for example, the dial member. The finger 132 is shown extending circumferentially and radially outward. In one example, the finger 132 extends circumferentially from a lateral sidewall 130A of the base 130 above the axial surface 131 of the flange 120 in spaced relationship to define a gap 133 therebetween. In this configuration, finger 132 can flex radially along its connection to the base 130. As shown in FIG. 32, the finger 132 is biased radially outward to place the tip 135 of finger 132 within the voids 137 defined between sides 123, 124 of the deformable members 222"". The finger tip 135 may be configured to provide enhanced sliding along the sides 123, 124. The deformable member 222"" may be molded, machined, or formed through additive manufacturing for attachment to the flange 120. In the example shown, the deformable member 222"" formed integrally with the flange 120 as a single unit, and some machining may be used for final shaping.

Button 56' is shown having a cylindrical outer wall 140, a proximal upper wall 142, and a distal end opening 144, defining a cup-shaped button. A cylindrical inner wall 146 that is in spaced relationship with the outer wall 140 may define an annular space 148.

The inner wall 146 may extend distally from the upper wall 142 and may have a recessed tip for mounting in alignment within an axial opening 139 formed in the flange 120 to place the force applicator in a radial location between the inner and outer walls 146, 140 against the deformable members 222"", as shown in FIG. 32. The upper wall 142 may be recessed from the top 141 of the outer wall 140 to define a mounting location for the piezoelectric sensor 100. The deformable members 222"" are shown extending distally from the distal surface 147 of the upper wall 142 within the annular space 148. In one example, the members 222"" are in physical contact with the upper wall 142 to better transmit deformation and/or vibration from contact with the force applicator. In another example, the members 222"" and the upper wall 142 integrally formed.

In the dose setting mode of operation, the user grasps and rotates dose button 56' relative to housing 12. Spring 68 biases dose button 56' and dial member 32 into fixed rotational engagement, such that the rotation of dose button 56' is transmitted to dial member 32 and flange 120. Because dose button 56' and dial member 32 rotate together during dose setting, sensor 100 of dose detection system 200"" may remain inactive.

In the dose dispensing mode of operation, the user applies an axial distal force to dose button 56'. The user's force overcomes the biasing force from spring 68 and releases dial member 32 to rotate relative to dose button 56' and housing 12. In the illustrated embodiment of FIG. 32, dial member 32 rotates counterclockwise relative to dose button 56, but this direction may vary. Because flange 120 is rotatably fixed to dial member 32, flange 120 also rotates counterclockwise relative to dose button 56'. The rotation of flange 120 relative to dose button 56' causes the deformable member 222"" (i.e., ratchet pawl) to flex radially inward away from its biased radial outward configuration as it rotates across consecutive force applicators 220"" (i.e., gear teeth). In the illustrated embodiment of FIG. 30, where the piezoelectric sensor 100 is coupled to the rigid force applicators 220"", a mechanical wave may be transmitted through dose button 56' to the piezoelectric sensor 100. It is also within the scope of the present disclosure for the piezoelectric sensor 100 to be coupled directly to the deformable member 222"", as shown for example in FIG. 15, such that the movement of the deformable member 222"" causes direct mechanical deformation of the piezoelectric sensor 100. Like the previous embodiments, the signal from the piezoelectric sensor 100 may be used to determine the amount of medication delivered from medication delivery device 10.

Additional information regarding the dose setting and dose dispensing modes of operation of medication delivery device 10 is provided above and in the previously incorporated U.S. Pat. Nos. 7,291,132 and 8,734,394.

Referring next to FIG. 20, an electronic control system 300 is provided for use with the corresponding dose detection system 200,200', 200", 200'", 200"". Control system 300 may communicate with each piezoelectric sensor 100 of dose detection system 200, 200', 200", 200'", 200"" to receive information regarding the sensed rotation of dose setting member 30 relative to housing 12, actuator 50, and/or another component of medication delivery device 10. Control system 300 may use the information from each piezoelectric sensor 100 to determine the amount of medication delivered from medication delivery device 10.

In the illustrated embodiment of FIG. 20, control system 300 is shown in combination with the second dose detection system 200'. Therefore, the following description relates to the second dose detection system 200'. However, it is understood that control system 300 may also be adapted for use with the first dose detection system 200 and other suitable dose detection systems.

The illustrative control system 300 of FIG. 20 includes a microcontroller unit (MCU) 302 located onboard housing 12 of medication delivery device 10. However, the location of MCU 302 may vary. For example, when control system 300 is adapted for use with the first dose detection system 200 of FIGS. 6-13, MCU 302 may be located on actuator 50 of medication delivery device 10. In other embodiments, at least a portion of MCU 302 may be located remotely from medication delivery device 10, such as on a remote server, a user's computer, or a user's smartphone.

The illustrative MCU 302 includes a processing core 304, a memory 306 (e.g., internal flash memory, on-board electrically erasable and programmable read-only memory (EEPROM), etc.), a power source 308 (e.g., coin cell battery), and a communication port 310. These components may be mounted to and communicate via a flexible printed circuit board (FPCB) 312. As discussed above, it is also within the scope of the present disclosure for certain elements of MCU 302, such as processing core 304 and/or memory 306, to be located remotely from medication delivery device 10.

MCU 302 communicates with voltage detector 108 of each piezoelectric sensor 100 or the single piezoelectric sensor when one is employed. Processing core 304 of MCU 302 is operative to perform the operations described herein, including determining the amount of medication delivered from medication delivery device 10 based on the information received from voltage detector 108 of each piezoelectric sensor 100. MCU 302 may store the detected amount of medication in memory 306. MCU 302 may also transmit the raw data from voltage detector 108 or the detected amount of medication from the on-board processing core 304 via communication port 310 to a paired remote device, such as a user's computer or smartphone. The information may be transmitted from communication port 310 via a wired or wireless communication protocol, such as a Bluetooth low energy (BLE) wireless communication protocol.

Figure 21:
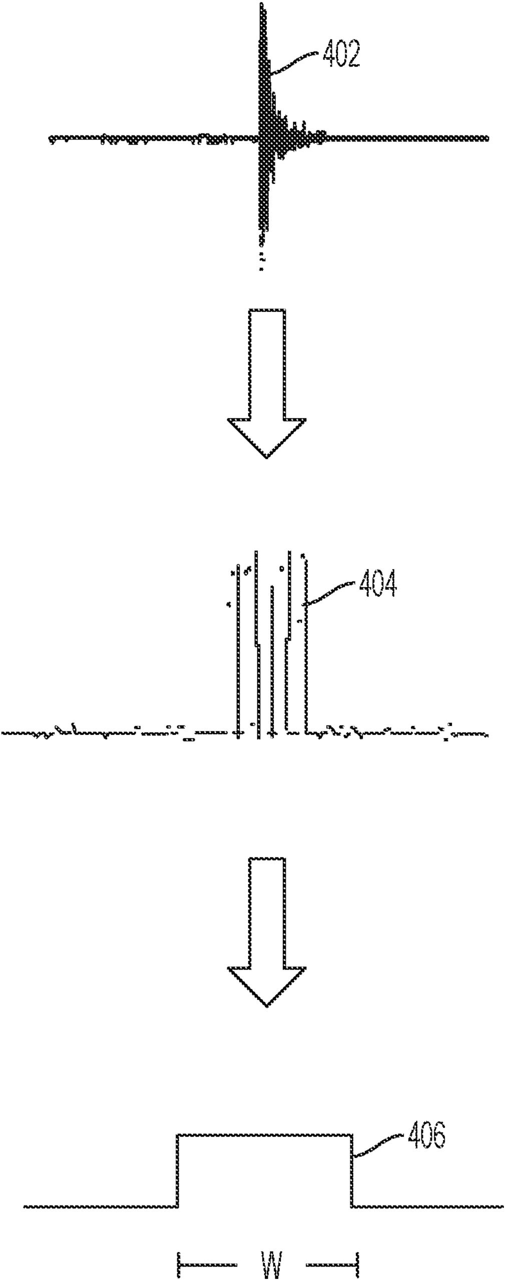
FIG. 21 is a diagram showing a signal conversion process performed by the control system of FIG. 20.

The system in FIG. 20 is shown with two signals 402, it is understood that the system may include only one signal 402. As shown in FIGS. 20 and 21, control system 300 may be configured to receive an analog piezoelectric signal 402 from voltage detector 108 of the piezoelectric sensor 100, which may be a substantially ring-shaped signal. Next, control system 300 may be programmed to convert the analog piezoelectric signal 402 to an intermediate digital signal 404, which may be a high-frequency signal that represents the time of the "click" or deformation event. Finally, control system 300 may be programmed to convert the intermediate digital signal 404 to a conditioned digital signal 406, which may be a single step/square wave with a predetermined width W representing a predetermined time, as described further below.

Figure 23:
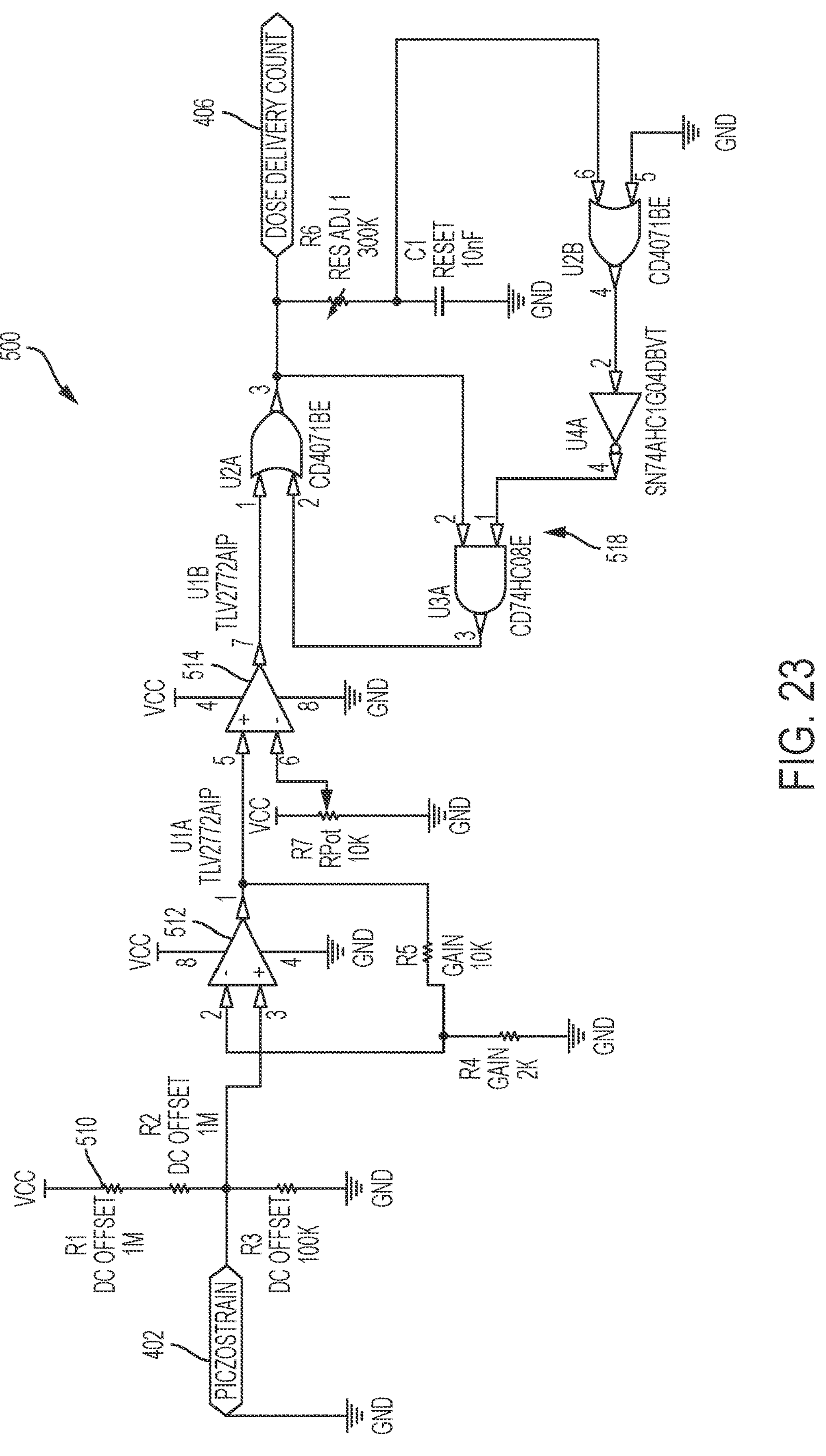
FIG. 23 is a circuit diagram of an electrical processing circuit performed by the control system of FIG. 20.

A signal processing logic or method 400 for use by control system 300 is shown in FIG. 22, and a corresponding signal processing circuit 500 is shown in FIG. 23. Logic 400 of FIG. 22 and the corresponding circuit 500 of FIG. 23 subject the analog piezoelectric signal 402 to a direct current (DC) voltage offset step 410 using resistors 510, followed by an amplification step 412 using amplifier 512, followed by an analog-to-digital conversion step 414 using comparator 514 to generate the intermediate digital signal 404. The signal 404 may be generated when the incoming voltage is at or above a predetermined voltage (e.g., 1.3 V). Alternatively, the signal 404 may be ignored at step 416 when the incoming voltage is less than the predetermined voltage. The intermediate digital signal 404 may be converted to the conditioned digital signal 406 by turning the signal "on" when initiating a timer at a timer initiation step 418 and turning the signal "off" when the timer expires after a predetermined time at a timer expiration step 420. The timing steps 418,420 may be performed using a resistance-capacitance (RC) timing loop 518. The predetermined time associated with the timing steps 418,420 may control the width W of the conditioned digital signal 406 (FIG. 21) and may be adjusted to match the time of each rotation and deformation event to minimize errors. Logic 400 of FIG. 22 and the corresponding circuit 500 of FIG. 23 may output a number corresponding to the number of digital signals 406 counted over a period of time.

In certain embodiments, control system 300 may be configured to distinguish the direction of rotation of dose setting member 30. For example, control system 300 may be configured to distinguish whether dose setting member 30 is rotating in a first direction during the dose setting operation or in a second direction during the dose dispensing operation. For purposes of determining the amount of medication actually delivered from medication delivery device 10, control system 300 may ignore the rotation of dose setting member 30 during the dose setting operation and only process the rotation of dose setting member 30 during the actual dose dispensing operation. Control system 300 may distinguish these directions using phase shifts or shift register coding, for example.

Figure 33:
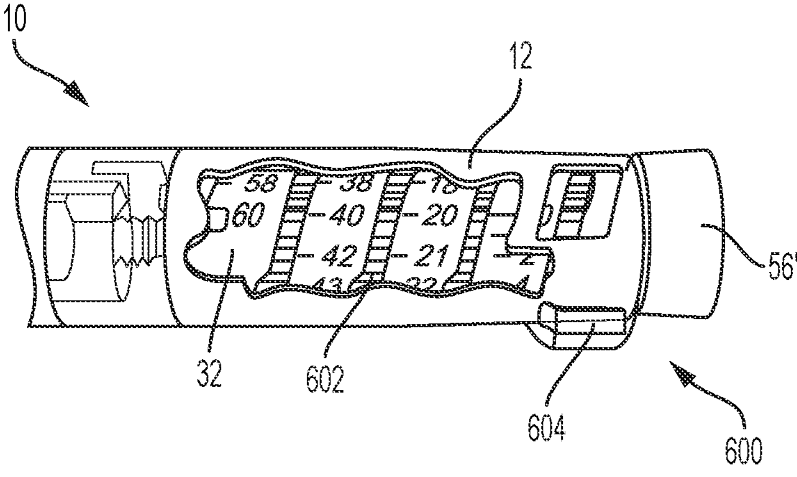
FIG. 33 is a cut-away side view of another exemplary medication delivery device of the present disclosure having a dose detection system with a potentiometer.
Figure 34:
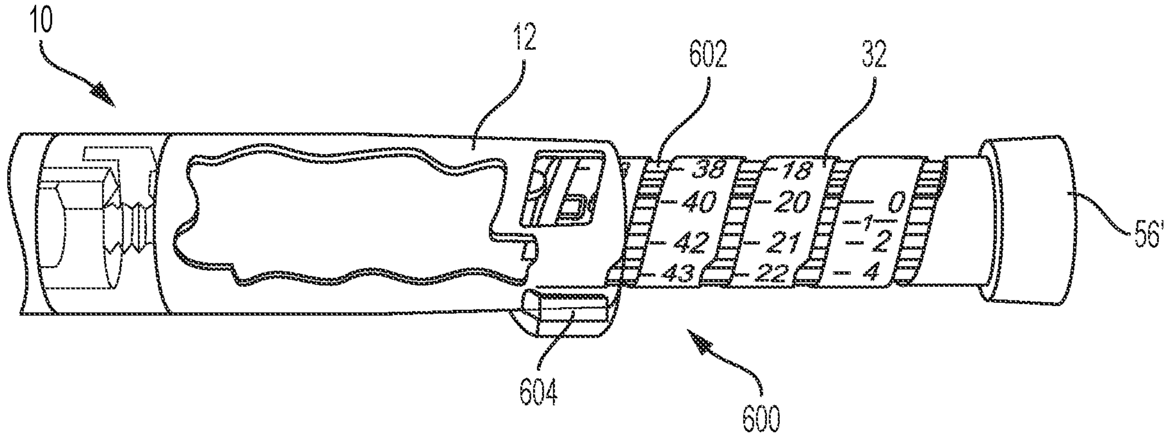
FIG. 34 is another cut-away side view of the medication delivery device of FIG. 33.

Referring finally to FIGS. 33-34, another dose detection system 600 is disclosed for use with medication delivery device 10 of the present disclosure or another suitable medication delivery device. The illustrative device 10 includes housing 12, dial member 32, and dose button 56', which are described further above. Dose detection system 600 includes a sensed component 602 in the form of a gear teeth or surface projections that extends radially outward in a helical pattern from dial member 32 and a sensing component 604 in the form of a multi-turn potentiometer having a shaft (not shown) that extends radially inward from housing 12 to mesh with gear 602. In operation, as dial member 32 rotates relative to housing 12, gear 602 causes the shaft of potentiometer 604 to rotate. Like the previous embodiments, a signal from the potentiometer 604 may be used to determine the amount of medication delivered from medication delivery device 10. The sensor 604 may also be other kinds of sensors, and the sensing components may comprise of other features that is detectable by the sensor, such as, including tactile, optical, electrical and magnetic properties. For example, the sensor 604 may be an optical source/sensor combination that emits light across the surface projections of sensed component 602 and the sensor 604 receives the reflected light and communicates to the controller the signal indicative of rotational movement. In one example, the sensor 604 may be an optical source that emits light across the sensed component 602 comprising a plurality of photodiodes and the sensed component 602 coupled to a circuit communicates to the controller the signal indicative of rotational movement. In another example, the sensor 604 may include a microswitch coupled to the device housing that is configured to deflect or switch due to contact with the surface projections of sensed component 602 and the sensor 604 communicates to the controller the signal indicative of rotational movement. In one example, the surface features are physical features which allow for detection of incremental movements as the dose setting member rotates relative to the actuator. In one example, the sensed component 602 is disposed in the helical groove is a linear potentiometer or a plurality of discrete potentiometers, and the sensing component 604 is a wiper sensor disposed from the device housing.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Various aspects are described in this disclosure, which include, but are not limited to, the following aspects:

1. A medication delivery device including: a device body having a longitudinal axis; an actuator that is movable relative to the device body during a dose setting operation and movable relative to the device body along the longitudinal axis during a dose dispensing operation to deliver a medication; a dose setting member that rotates relative to the device body during the dose dispensing operation; and a dose detection system configured to detect rotation of the dose setting member relative to the actuator during the dose dispensing operation, the dose detection system including a piezoelectric sensor.

2. The medication delivery device of aspect 1, wherein the dose detection system includes: a ratchet finger coupled to the dose setting member; and a ratchet gear teeth coupled to the actuator, the ratchet gear teeth contactable with the ratchet finger during relative rotation.

3. The medication delivery device of any one of the previous aspects, wherein the piezoelectric sensor is mounted to the actuator.

4. The medication delivery device of any one of the previous aspects, wherein: a ratchet finger having a base coupled to an axial surface of the dose setting member, the ratchet finger extending circumferentially above the axial surface and in a space relationship with the axial surface, the ratchet finger configured to flex radially; and a ratchet gear teeth coupled to a dose button of the actuator, the ratchet gear teeth extending longitudinally along an inner wall of the dose button, the ratchet gear teeth contactable with the ratchet finger during relative rotation to cause the ratchet finger to flex radially inward.

5. The medication delivery device of aspect 4, wherein the dose detection system includes a controller in electrical communication with the piezoelectric sensor, the controller configured to: receive an analog signal generated by the piezoelectric sensor; convert the analog signal to a digital signal; and determine a unit of rotational movement of the dose setting member from the digital signal, the unit of rotational movement indicative of an amount of dose dispensed during the dose dispensing operation.

6. The medication delivery device of any one of the previous aspects, further including a voltage detector configured to receive a signal from the piezoelectric sensor.

7. The medication delivery device of aspect 6, further including a communication port configured to send information from the voltage detector to a remote device.

8. The medication delivery device of any one of the previous aspects, further including a reservoir containing the medication and a piston coupled to the actuator, the piston traveling through the reservoir in the dose dispensing operation to deliver the medication from the reservoir.

9. A medication delivery device including: a device body having a longitudinal axis; an actuator that rotates relative to the device body during a dose setting operation and moves axially relative to the device body along the longitudinal axis during a dose dispensing operation to deliver a medication; a dose setting member that is fixedly coupled to the actuator during the dose setting operation and that rotates relative to the actuator during the dose dispensing operation; and a piezoelectric sensor configured to detect rotation between the dose setting member and the actuator during the dose dispensing operation.

10. The medication delivery device of aspect 9, wherein the piezoelectric sensor is inactive during the dose setting operation.

11. The medication delivery device of any one of the aspects 9-10, wherein: the actuator includes a ratchet gear with a plurality of teeth; the dose setting member includes a ratchet pawl; and the piezoelectric sensor detects rotation of the ratchet pawl across each tooth of the ratchet gear.

12. A medication delivery device including: a device body having a longitudinal axis; a dose setting member coupled to the device body and rotatable relative to the device body during a dose dispensing operation; an actuator coupled to the device body and movable relative to the device body during the dose dispensing operation; and a dose detection system configured to detect rotation of the dose setting member during the dose dispensing operation, the dose detection system including: at least one deformable member; a piezoelectric sensor coupled to the at least one deformable member; and at least one force applicator configured to apply a mechanical force to the at least one deformable member and deform the piezoelectric sensor during the dose dispensing operation.

13. The medication delivery device of aspect 12, further including a control system in communication with the dose detection system, the control system being programmed to determine an amount of delivered medication based on the deformation of the piezoelectric sensor.

14. The medication delivery device of any one of the aspects 12-13, wherein the at least one force applicator is rotatable relative to the at least one deformable member during the dose dispensing operation.

15. The medication delivery device of any one of the aspects 12-14, wherein the at least one force applicator is rotationally coupled to the dose setting member such that the at least one force applicator and the dose setting member rotate together during the dose dispensing operation.

16. The medication delivery device of aspect 15, wherein the at least one force applicator includes a plurality of teeth arranged in a helical pattern on an outer surface of the dose setting member.

17. The medication delivery device of aspect 15, wherein the at least one force applicator includes a finger that extends from the dose setting member in one of an axially proximal direction and a radially outward direction.

18. The medication delivery device of any one of the aspects 12-17, wherein the at least one deformable member is coupled to one of the device body and the actuator.

19. The medication delivery device of aspect 18, wherein the at least one deformable member includes a plurality of teeth arranged on an inner surface of the device body.

20. The medication delivery device of aspect 18, wherein the at least one deformable member includes a plurality of teeth arranged on a distal surface of the actuator.

21. The medication delivery device of any one of the aspects 12-20, wherein the at least one force applicator deforms the piezoelectric sensor in an axial direction that is substantially parallel to the longitudinal axis.

22. The medication delivery device of any one of the aspects 12-21, wherein the at least one force applicator deforms the piezoelectric sensor in a radially outward direction that is substantially perpendicular to the longitudinal axis.

23. The medication delivery device of any one of the aspects 12-22, wherein the dose detection system is a modular component that is removably coupled to the device body.

24. The medication delivery device of any one of the aspects 12-23, wherein the dose detection system is an integral component that is permanently coupled to the device body.

25. The medication delivery device of any one of the aspects 12-24, wherein: the at least one deformable member is flexible; and the at least one force applicator is rigid.

26. The medication delivery device of any one of the aspects 12-25, wherein: during a dose setting operation, the dose setting member is rotationally coupled to the actuator such that the dose setting member and the actuator rotate together relative to the device body; and during the dose dispensing operation, the dose setting member is rotationally uncoupled from the actuator such that the dose setting member rotates relative to the actuator.

27. The medication delivery device of any one of the aspects 12-26, wherein the device body includes a reservoir having a medication.

The invention claimed is:

1. A medication delivery device comprising:

a device body having a longitudinal axis;

a dose setting member coupled to the device body and rotatable relative to the device body during a dose dispensing operation;

an actuator coupled to the device body and movable relative to the device body during the dose dispensing operation; and a dose detection system configured to detect rotation of the dose setting member during the dose dispensing operation, the dose detection system comprising:

a plurality of surface projections arranged on an outer surface of the dose setting member, and a multi-turn potentiometer having a shaft that meshes with the plurality of surface projections such that rotation of the dose setting member drives rotation of the shaft.

2. The medication delivery device of claim 1, wherein the shaft of the potentiometer extends radially inward from the device body.

3. The medication delivery device of claim 1, further comprising a control system in communication with the dose detection system, the control system being programmed to determine an amount of delivered medication based on the rotation of the shaft of the potentiometer.

4. The medication delivery device of claim 1, wherein the plurality of surface projections are arranged in a helical pattern on the outer surface of the dose setting member.

5. The medication delivery device of claim 1 wherein the device body includes a reservoir having a medication.

* * * * *